(12) United States Patent
Brahmbhatt et al.

(10) Patent No.: US 9,731,011 B2
(45) Date of Patent: Aug. 15, 2017

(54) COMBINATION TUMOR TREATMENT WITH DRUG-LOADED, BISPECIFIC LIGAND-TARGETED MINICELLS AND INTERFERON-GAMMA

(71) Applicant: EnGeneIC Molecular Delivery Pty Ltd, Lane Cove West, Sydney (AU)

(72) Inventors: Himanshu Brahmbhatt, Sydney (AU); Jennifer MacDiarmid, Sydney (AU)

(73) Assignee: EnGeneIC Molecular Delivery Pty Ltd, Sydney (AU)

( * ) Notice: Subject to any disclaimer, the term of this patent is extended or adjusted under 35 U.S.C. 154(b) by 0 days.

(21) Appl. No.: 14/506,138

(22) Filed: Oct. 3, 2014

(65) Prior Publication Data

US 2015/0098897 A1 Apr. 9, 2015

Related U.S. Application Data

(60) Provisional application No. 61/887,258, filed on Oct. 4, 2013.

(51) Int. Cl.
| | | |
|---|---|---|
| *A61K 39/44* | (2006.01) | |
| *A61K 38/12* | (2006.01) | |
| *A61K 31/704* | (2006.01) | |
| *A61K 38/21* | (2006.01) | |
| *A61K 39/395* | (2006.01) | |
| *C07K 16/28* | (2006.01) | |
| *C07K 16/44* | (2006.01) | |
| *A61K 35/74* | (2015.01) | |
| *A61K 45/06* | (2006.01) | |

(52) U.S. Cl.
CPC ............ *A61K 39/44* (2013.01); *A61K 31/704* (2013.01); *A61K 35/74* (2013.01); *A61K 38/217* (2013.01); *A61K 39/3955* (2013.01); *A61K 39/39583* (2013.01); *A61K 45/06* (2013.01); *C07K 16/2863* (2013.01); *C07K 16/44* (2013.01); *C07K 2317/31* (2013.01)

(58) Field of Classification Search
None
See application file for complete search history.

(56) References Cited

U.S. PATENT DOCUMENTS

| 7,183,105 | B2 | 2/2007 | Sabbadini et al. |
| 8,591,862 | B2 | 11/2013 | Brahmbhatt et al. |
| 2006/0194951 | A1* | 8/2006 | Jensen ............ A61K 47/48215 530/351 |
| 2007/0116767 | A1* | 5/2007 | Mohapatra ............ A61K 9/0043 424/489 |
| 2007/0237744 | A1 | 10/2007 | Brahmbhatt et al. |
| 2008/0038296 | A1 | 2/2008 | Brahmbhatt et al. |
| 2008/0051469 | A1 | 2/2008 | Brahmbhatt et al. |
| 2011/0275585 | A1 | 11/2011 | Brahmbhatt et al. |
| 2014/0093954 | A1* | 4/2014 | Giacalone .............. C07K 14/33 435/317.1 |

FOREIGN PATENT DOCUMENTS

| CA | 2 803 995 | 3/2006 |
| WO | WO 98/02446 | 1/1998 |
| WO | WO 00/67776 | 11/2000 |
| WO | WO 03/033519 A2 | 4/2003 |
| WO | WO 2004/113507 A1 | 12/2004 |
| WO | WO 2005/056749 A2 | 6/2005 |
| WO | WO 2005/079854 A1 | 9/2005 |
| WO | WO 2006/021894 * | 2/2006 |
| WO | WO 2006/021894 A2 | 3/2006 |
| WO | WO 2008/012695 A2 | 1/2008 |
| WO | WO 2009/027830 A2 | 3/2009 |
| WO | WO 2013/088250 A1 | 6/2013 |

OTHER PUBLICATIONS

Hoppner (Horm Re. 2002, 58 Suppl. 3:7-15).*
Quintiero et al., American Association for Cancer Research, 2005; 11: 1608-1617.*
Zaidi et al., Clin Cancer Res, 2011; 17(19): 6118-6124.*
van der Meel, Advanced Drug Delivery Reviews, 2013; 65: 1284-1298.*
Britton et al., "Characterization of a prokaryotic SMC protein involved in chromosome partitioning", Genes & Development, 1998, vol. 12, pp. 1254-1259.
Caplen et al., "Short Interfering RNA (siRNA)-Mediated RNA Interference (RNAi) in Human Cells", Annals New York Academy of Sciences, 2003, 1002, pp. 56-62.
Caplen, "RNAi as a gene therapy approach", Expert Opin. Biol. Ther., 2003, Vo. 3, No. 4, pp. 575-586.
Caravella et al., "Design of next-generation protein therapeutics," Curr. Opin. Chem. Biol. 14: pp. 520-528 (2010). [Abstract].
Chu et al., Translation Repression in Human Cells by MicroRNA-Induced Gene Silencing Requires RCK/p54, *PLoS Biology* 4: pp. 1122-1136 (2006).
Da Silva et al., HER3 and downstream pathways are involved in colonization of brain metastases from breast cancer, *Breast Cancer Res.* 12: R46 (1-13) (2010).

(Continued)

*Primary Examiner* — Padma V Baskar
(74) *Attorney, Agent, or Firm* — Foley & Lardner LLP

(57) ABSTRACT

Compositions and methods are provided for cancer treatments. The methodology entails, for instance, administering to a cancer patient a first composition comprising a plurality of bacterially derived intact minicells or intact killed bacterial cells, each of which encompasses an anti-neoplastic agent and carries a bispecific ligand on the surface, the ligand having specificity for a mammalian cell component, and a second composition comprising interferon-gamma (IFN-gamma) or an agent that increases the expression of IFN-gamma in the subject. The compositions include the first composition and the second composition as described, optionally with additional anti-neoplastic agents.

16 Claims, 9 Drawing Sheets

(9 of 9 Drawing Sheet(s) Filed in Color)

(56) References Cited

OTHER PUBLICATIONS

D'Angiolella et al., "The Cyclin F-Ribonucleotide Reductase M2 axis controls genome integrity and DNA repair," Cell: 149:1023-1034 (2012).
De Boer et al., "Roles of MinC and MinD in the Site-Specific Septation Block Mediated by the MinCDE System of Escherichia coli", Journal of Bacteriology, 1992, vol. 174, No. 1, pp. 63-70.
Debinski et al., "Molecular Expression Analysis of Restrictive Receptor for Interleukin 13, a Brain Tumor-associated Cancer/Testis Antigen," Mol. Med. 6: 440-449 (2000).
Debinski et al., "Expression of a restrictive receptor for interleukin 13 is associated with glial transformation," J. Neurooncol. 48: 103-111 (2000). [Abstract].
Duan et al., "Inhibition of ABCB1 (MDR1) and ABCB4 (MDR3) expression by small interfering RNA and reversal of paclitaxel resistance in human ovarian cancer cells", Molecular Cancer Therapeutics, 2004, vol. 3, No. 7, pp. 833-838.
Duxbury el al., "Systemic siRNA-Mediated Gene Silencing a New Approach to Targeted Therapy of Cancer," Ann. Surg. 240: 667-674 (2004).
Goh et al., "Endocytosis of Receptor Tyrosine Kinases," Cold Spring Harb. Perspect. Biol. 5: a017459, 17 pages (2013).
Gregory et al., "MicroRNA Biogenesis: Isolation and Characterization of the Microprocessor Complex Methods in Molecular Biology," vol. 342, pp. 33-47 (2006). [Abstract].
Harry, "Bacterial cell division: regulating Z-ring formation", Molecular Microbiology, 2001, vol. 40, No. 4, pp. 795-803.
Hershey, "IL-13 receptors and signaling pathways: an evolving web," J. Allergy Clin. Immunol., vol. 111, pp. 677-690 (2003).
Hiraga et al., "Chromosome Partitioning in Escherichia coli: Novel Mutants Producing Anucleate Cells", Journal of Bacteriology, 1989, vol. 171, No. 3, pp. 1496-1505.
Hu et al., "Topological regulation of cell division in Escherichia coli involves rapid pole to pole oscillation of the division inhibitor MinC under the control of MinD and MinE", Molecular Microbiology, 1999, vol. 34, No. 1, pp. 82-90.
Iftode et al., Replication protein A (RPA): the eukaryotic SSB, Crit. Rev. Biochem. Mol. Biol. 34: pp. 141-180 (1999). [Abstract].
Ireton et al., "spoOJ Is Required for Normal Chromosome Segregation as well as the Initiation of Sporulation in Bacillus subtilis", Journal of Bacteriology, 1994, vol. 176, No. 17, pp. 5320-5329.
Jarboe et al., "Expression of Interleukin-13 Receptor α2 in Glioblastoma Multiforme: Implications for Targeted Therapies," Cancer Res. 67: 7983-7986 (2007).
Khalil et al., "Many human large intergenic noncoding RNAs associate with chromatin-modifying complexes and affect gene expression," Proc Nat'l Acad. USA 106: pp. 11667-11672 (2009).
Kloke et al., "A prospective randomized comparison of single-agent interferon (IFN)-alpha with the combination of IFN-alpha and low-dose IFN-gamma in chronic myelogenous leukaemia," Eur. J. Haematol. 48: 93-8 (1992). [Abstract].
Kota et al., "Therapeutic delivery of miR-26a inhibits cancer cell proliferation and induces tumor-specific apoptosis," Cell 137: 1005-1017 (2009).
Lemmon et al., "Cell signaling by receptor-tyrosine kinases," Cell 141(7): 1117-134 (2010).

MacDiarmid et al. (2009) "Sequential treatment of drug-resistant tumors with targeted minicells containing siRNA or a cytotoxic drug" Nature Biotechnology 27(7):643-651.
Nieth et al., "Modulation of the classical multidrug resistance (MDR) phenotype by RNA interference (RNAi)", FEBS Letters 545 (2003) pp. 144-150.
Oh et al., "siRNA delivery systems for cancer treatment," Advanced Drug Delivery Rev. 61: 850-62 (2009). [Abstract].
Okada et al., "Cytoplasmic Axial Filaments in Escherichia coli Cells: Possible Function in the Mechanism of Chromosome Segregation and Cell Division", Journal of Bacteriology, Feb. 1994, pp. 917-922.
Raskin et al., "MinDE-Dependent Pole-to-Pole Oscillation of Division Inhibitor MinC in Escherichia coli", Journal of Bacteriology. vol. 181, No. 20, Oct. 1990, pp. 6410-6424.
Reeve et al. "Bacteriophage SPO1-Induced Macromolecular Synthesis in Minicells of Bacillus subtilis", Journal of Virology, vol. 15, No. 6, Jun. 1975, pp. 1308-1316.
Rice et al., The next generation of Positron Emission Tomography Radiopharmaceuticals in Oncology. Semin. Nucl. Med., vol. 41, pp. 265-282 (2011).
Sioud, "Therapeutic siRNAs", Trends in Pharmacological Sciences, vol. 25, No. 1, Jan. 2004, pp. 22-28.
Stewart et al., "Genetic and Morphological Characterization of an Escherichia coli Chromosome segregation Mutant", Journal of Bacteriology, Jul. 1992, vol. 174, No. 13, pp. 4513-4516.
Tanpure et al., "Synthesis of structurally diverse benzosuberene analogues and their biological evaluation as anti-cancer agents," Bioorg. Med. Chem. 21: 8019-32 (2013).
Wandl et al., "Treatment of chronic myelogenous leukemia with different cytokines," Semin. Oncol. 19: 88-94 (1992). [Abstract].
Wykosky et al., "Interleukin-13 Receptor α2, EphA2, and Fos-Related Antigen 1 as Molecular Denominators of High-Grade Astrocytomas and Specific Targets for Combinatorial Therapy," Clin Cancer Res. 14: 199-208 (2008).
Yagüe et al., "Complete reversal of multidrug resistance by stable expression of small interfering RNAs targeting MDR1", Gene Therapy 2004, 11, 1170-1174.
Jennifer A. MacDiarmid et al., "Bacterially-Derived Nanocells for Tumor-Targeted Delivery of Chemotherapeutics and Cell Cycle Inhibitors," Cell Cycle, Sep. 7, 2007, vol. 6, No. 7, pp. 2099-2105.
Jennifer A. MacDiarmid et al., "Bacterially Derived 400 nm Particles for Encapsulation and Cancer Cell Targeting of Chemotherapeutics", Cancer Cell 11, May 2007, pp. 431-445.
International Search Report issued in related International Patent Application No. PCT/IB2014/002824, dated Feb. 13, 2015.
International Preliminary Report on Patentability issued in related International Patent Application No. PCT/IB2014/002824, dated Apr. 14, 2016.
Hussner et al., "Regulation of Interferon-Inducible Proteins by Doxorubicin via Interferon—Janus Tyrosine Kinase-Signal Transducer and Activator of Transcription Signaling in Tumor Cells," Molecular Pharmacology, vol. 81, No. 5, pp. 679-688 (2012).
Vincenzi et al., "Angiogenesis modifications related with cetuximab plus irinotecan as anticancer treatment in advanced colorectal cancer patients," Ann Oncol., vol. 17, No. 5, pp. 835-841 (2006).
MacDiarmid et al., "Sequential Treatment of Drug-Resistant Tumors with Targeted Minicells containing SiRNA or a cytotoxic drug," Nature Biotechnology, vol. 27, No. 7, pp. 643-651 (2009).
Search Report and Written Opinion issued in related Singapore Patent Application No. 11201602429Q, dated Mar. 16, 2017.

* cited by examiner

COMBINATION TUMOR TREATMENT WITH DRUG-LOADED, BISPECIFIC LIGAND-TARGETED MINICELLS AND INTERFERON-GAMMA

CROSS-REFERENCE TO RELATED APPLICATION

This application claims priority from U.S. Provisional Patent Application No. 61/887,258, filed Oct. 4, 2013. The contents of that application are incorporated herein by reference in their entirety.

BACKGROUND

Currently, most drugs used for treating cancer are administered systemically. Although systemic delivery of cytotoxic anticancer drugs plays a crucial role in cancer therapeutics, it also engenders serious problems. For instance, systemic exposure of normal tissues/organs to the administered drug can cause severe toxicity. This is exacerbated by the fact that systemically delivered cancer chemotherapy drugs often must be delivered at very high dosages to overcome poor bioavailability of the drugs and the large volume of distribution within a patient. Also, systemic drug administration can be invasive, as it often requires the use of a secured catheter in a major blood vessel. Because systemic drug administration often requires the use of veins, either peripheral or central, it can cause local complications such as phlebitis. Extravasation of a drug also can lead to vesicant/tissue damage at the local site of administration, such as is commonly seen upon administration of vinca alkaloids and anthracyclines.

Another challenge in cancer therapy is evasion by tumor cells from immune surveillance. Interactions between the immune system and malignant cells play an important role in tumorigenesis. Failure of the immune system to detect and reject transformed cells may lead to cancer development. Tumors use multiple mechanisms to escape from immune-mediated rejection. Many of these mechanisms are now known on a cellular and molecular level. Despite this knowledge, cancer immunotherapy is still not an established treatment in the clinic.

SUMMARY

The present inventors discovered that an animal undergoing cancer therapy with anti-neoplastic drug-loaded, bispecific antibody-targeted, minicells exhibits a greater anti-tumor response to the drug when the animal is suffering from a concomitant viral infection. Further investigation revealed that the observed enhancement in the therapeutic efficacy of an anti-cancer drug in this context arose from synergism between the tumor-killing capability of the administered, drug-loaded, bispecific antibody-targeted minicells and an activated host-immune response against tumor cells, itself due to increased expression of interferon-gamma (IFN-gamma or IFNγ) that the viral infection triggered.

IFN-gamma itself has been investigated for its potential anti-neoplastic use, both in monotherapy and in combination with other anti-neoplastic agents. Such investigations have not led to clinical success, however. For instance, the combination treatment of IFN-alpha and IFN-gamma failed to exhibit an improvement over treatment with IFN-alpha alone. See, e.g., Kloke et al., *Eur. J. Haematol.* 48: 93-8 (1992), and Wandl et al., *Semin. Oncol.* 19: 88-94 (1992). The only IFN-gamma indications approved by the U.S. Food and Drug Administration (FDA) are for treating chronic granulomatous disease (CGD) and severe malignant osteopetrosis (bone disease).

In one of its aspects, therefore, the present disclosure provides a method for treating a tumor in a subject. The method entails administering to the subject (A) a first composition comprising a plurality of bacterially derived intact minicells and/or killed bacterial cells, each of which minicells and killed cells encompasses an anti-neoplastic agent and are targeted to a tumor cell surface receptor via a ligand attached to the minicell surface, and (B) a second composition comprising IFN-gamma or an agent that increases the expression or activity of IFN-gamma in the subject.

In some aspects, the second composition comprises IFN-gamma protein, in particular a pharmaceutically suitably purified IFN-gamma protein. In some aspects, the second composition comprises a viral vaccine. In some aspects, the second composition comprises a nucleic acid encoding IFN-gamma.

In some aspects, the first composition comprises from about $10^9$ to about $10^{10}$ minicells or killed bacterial cells.

In some aspects, the anti-neoplastic agent is a radionuclide. In some aspects, the anti-neoplastic agent is a chemotherapy drug. In some aspects, the anti-neoplastic agent is a functional nucleic acid or a polynucleotide encoding a functional nucleic acid. In some aspects, the functional nucleic acid inhibits a gene that promotes tumor cell proliferation, angiogenesis or resistance to chemotherapy and/ or that inhibits apoptosis or cell cycle arrest. In some aspects, the functional nucleic acid is selected from siRNA, miRNA, shRNA, lincRNA, antisense RNA, or ribozyme.

Also provided are packages, products or kits comprising a first composition comprising a plurality of bacterially derived intact minicells or intact killed bacterial cells, each of which encompasses an anti-neoplastic agent and carries a ligand on the surface wherein the ligand has specificity to a non-phagocytic mammalian cell surface receptor, and a second composition comprising interferon-gamma (IFN-gamma) or an agent that increases the expression of IFN-gamma in the subject.

In another embodiment, provided is a composition comprising (a) a plurality of bacterially derived intact minicells or intact killed bacterial cells, each of which encompasses an anti-neoplastic agent and carries a ligand on the surface wherein the ligand has specificity to a non-phagocytic mammalian cell surface receptor, and (b) IFN-gamma or an agent that increases the expression of IFN-gamma in the subject.

Other objects, features, and advantages are apparent from the following description. The detailed description and specific examples are given for illustration only, since various changes and modifications within the spirit and scope of the particular embodiments are apparent from this description.

BRIEF DESCRIPTION OF THE DRAWINGS

The patent or application file contains at least one drawing executed in color. Copies of this patent or patent application publication with color drawing(s) will be provided by the Office upon request and payment of necessary fee.

These charts show that the response of the tumor to the drug was much greater when serum concentrations of IFN-gamma were elevated.

Figure 2:
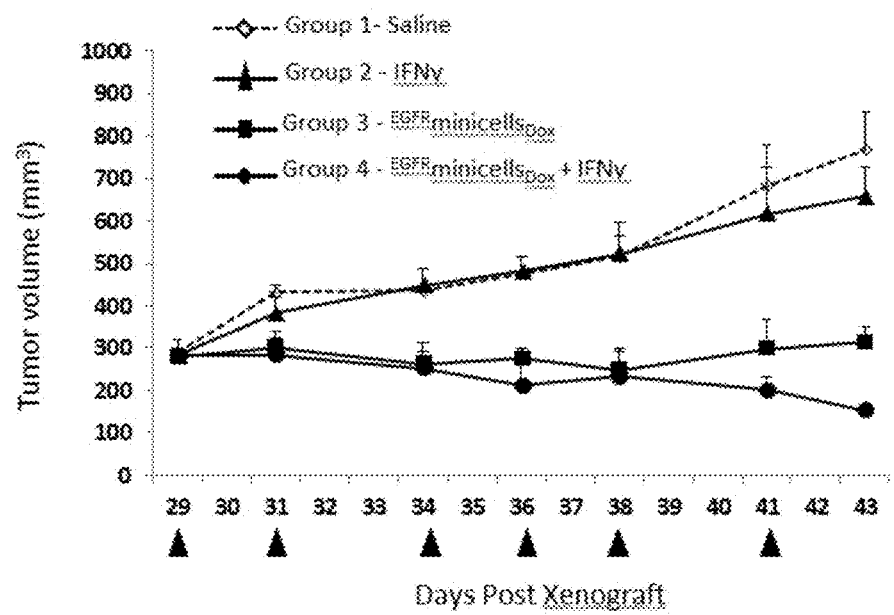

FIG. 2 illustrates the effects of combined treatment, with IFN-gamma and bispecific ligand-targeted and doxorubicin-packaged intact minicells, of human alveolar adenocarcinoma tumor xenografts, established in 6 week-old female athymic nude mice with a tumor size of about 285 mm$^3$. Group 1 mice received saline, Group 2 mice received IFN-gamma only, Group 3 mice received $^{EGFR}$minicells$_{Dox}$, and Group 4 mice received $^{EGFR}$minicells$_{Dox}$ and IFN-gamma. In this example and those to follow, the triangles below the x axis indicate the time of dosing.

Figure 3:
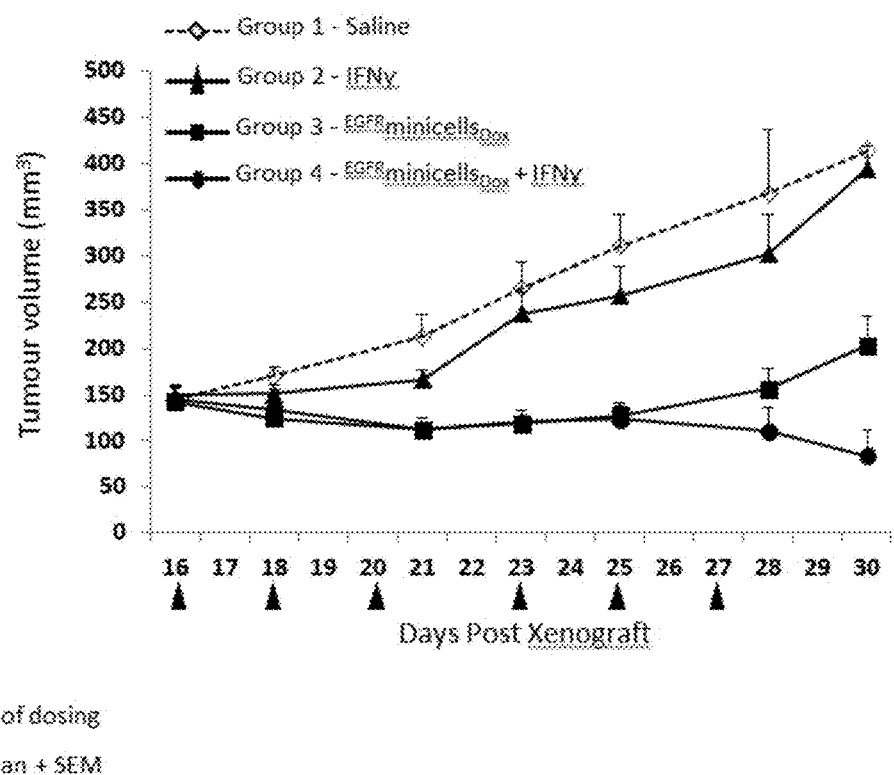

FIG. 3 depicts the effects of combined treatment, with IFN-gamma and bispecific ligand-targeted and doxorubicin-packaged, intact minicells, of human breast tumor xenografts established in 6 week-old female athymic nude mice with a moderate tumor size, about 145 mm$^3$. Group 1 mice received saline, Group 2 mice received IFN-gamma only, Group 3 mice received $^{EGFR}$minicells$_{Dox}$, and Group 4 mice received $^{EGFR}$minicells$_{Dox}$ and IFN-gamma.

Figure 4:
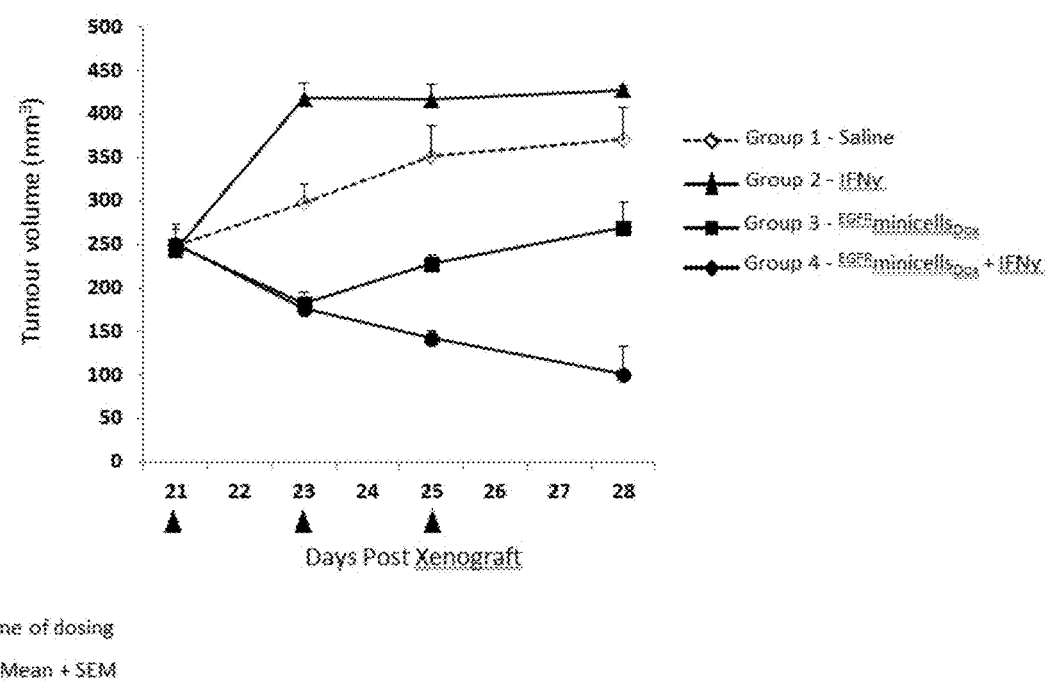

FIG. 4 illustrates the effects of combined treatment, with IFN-gamma and bispecific ligand-targeted and doxorubicin-packaged intact minicells, of human breast tumor xenografts established in 6 week-old female athymic nude mice with large tumor size, about 250 mm$^3$. Group 1 mice received saline, Group 2 mice received IFN-gamma only, Group 3 mice received $^{EGFR}$minicells$_{Dox}$, and Group 4 mice received $^{EGFR}$minicells$_{Dox}$ and IFN-gamma.

Figure 5:
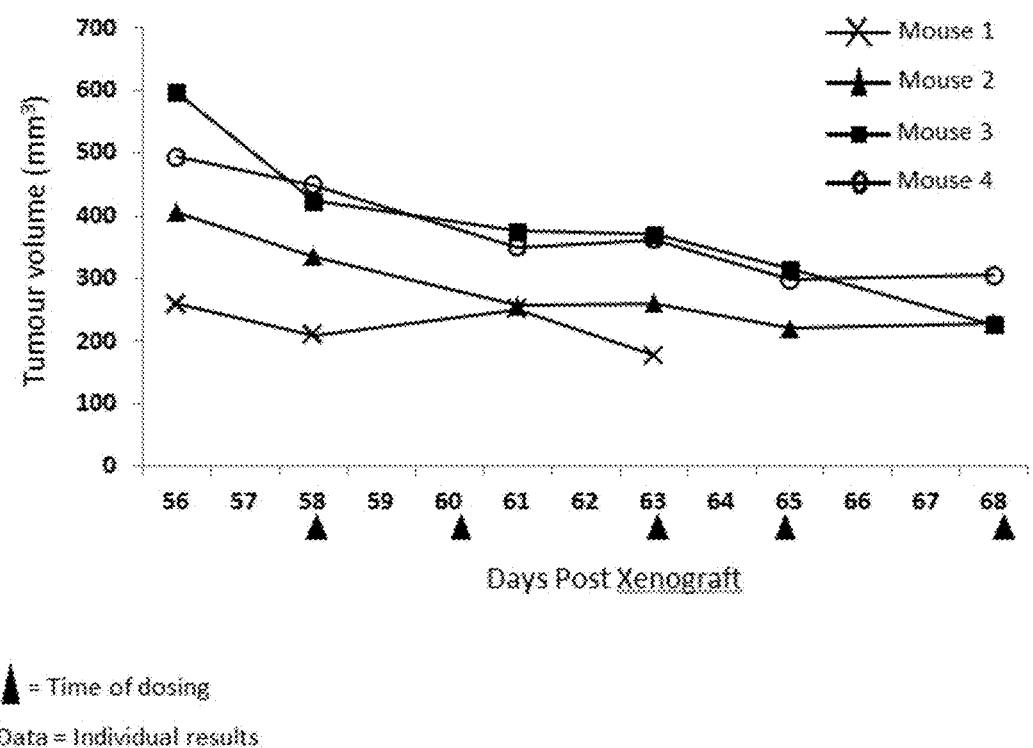

FIG. 5 depicts the effects of combined treatment, with IFN-gamma and bispecific ligand-targeted and doxorubicin-packaged intact minicells, of human breast tumor xenografts established in 6 week-old female athymic nude mice with a very large tumor size, between about 265 and about 600 mm$^3$. All four mice received $^{EGFR}$minicells$_{Dox}$ and IFN-gamma.

Figure 6:
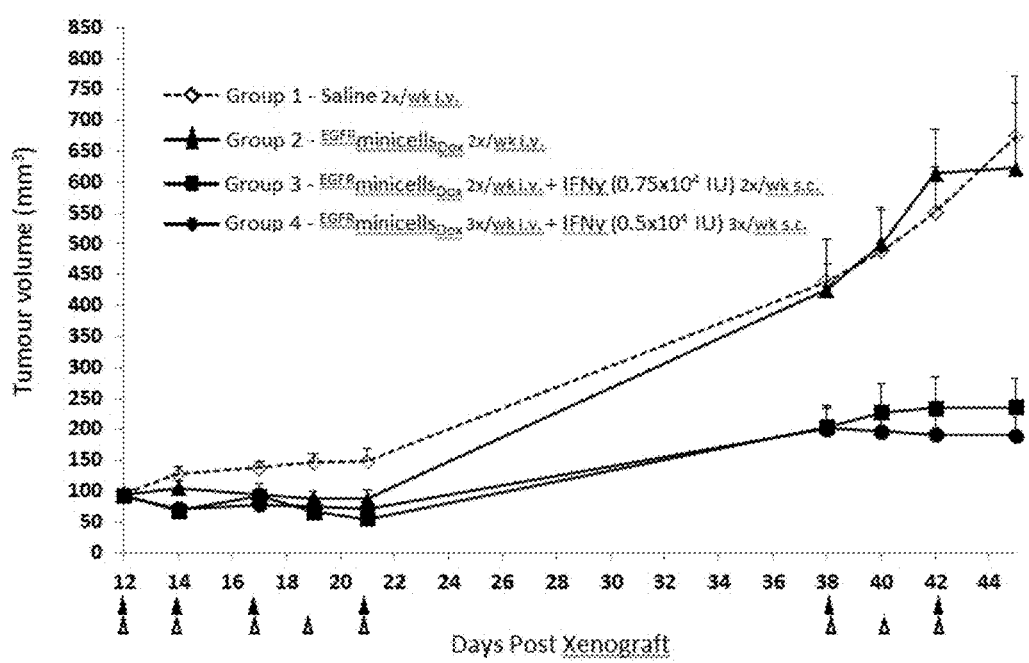

FIG. 6 portrays the effects of combined treatment, with IFN-gamma (two different doses) and bispecific ligand-targeted and doxorubicin-packaged intact minicells, of human alveolar adenocarcinoma tumor xenografts established in 6 week-old female athymic nude mice with a tumor size of about 100 mm$^3$. Group 1 mice received saline, Group 2 mice received $^{EGFR}$minicells$_{Dox}$, Group 3 mice received $^{EGFR}$minicells$_{Dox}$ and 0.75×10$^4$ IU of IFN-gamma, twice per week, and Group 4 mice received $^{EGFR}$minicells$_{Dox}$ and 0.5×10$^4$ IU of IFN-gamma, three times per week.

Figure 7:
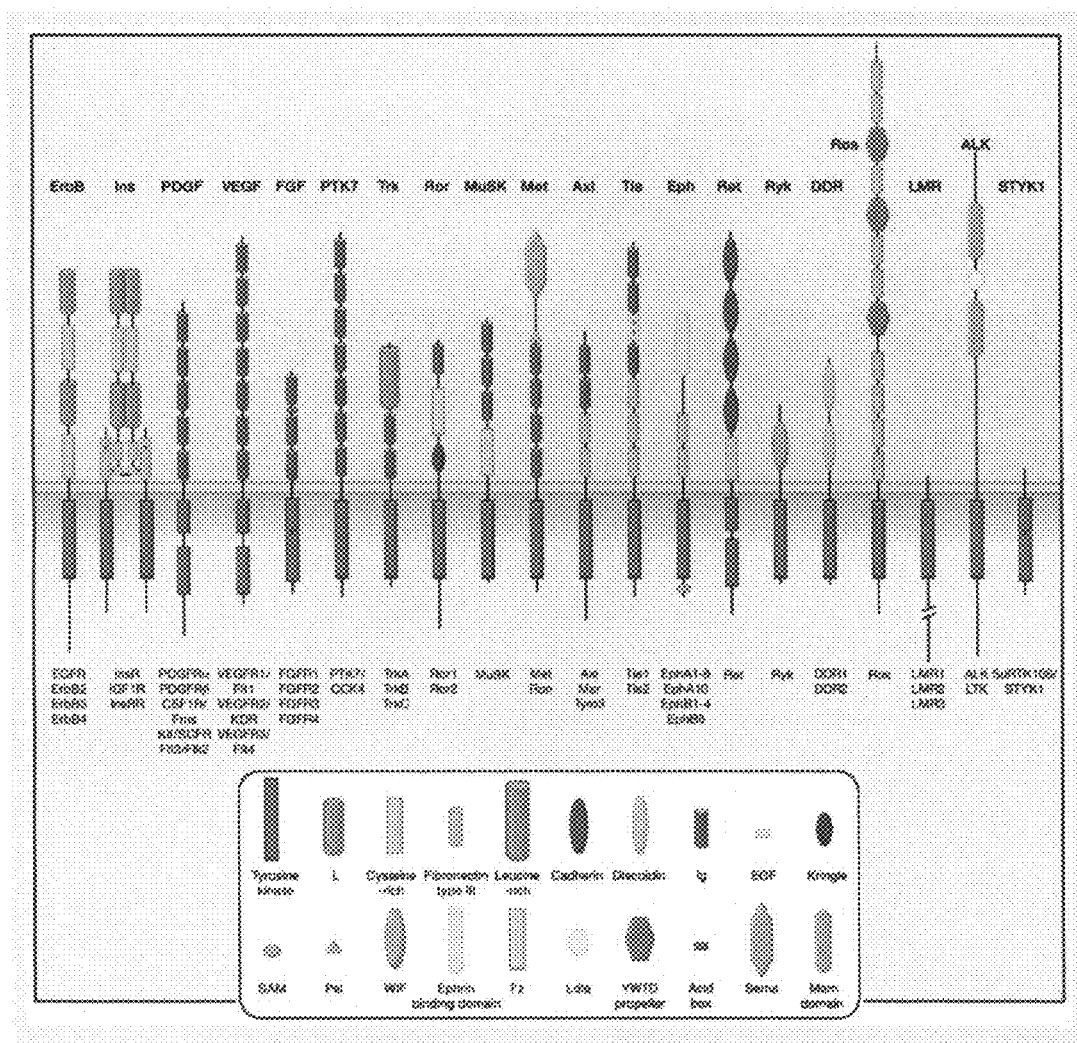

FIG. 7 illustrates 20 subfamilies and 58 members of human receptor tyrosine kinases (excerpted from Lemmon and Schlessinger, *Cell* 141: 1117-134 (2010)).

DETAILED DESCRIPTION

As noted above, the inventors determined that administering anti-neoplastic drug-loaded, bispecific antibody-targeted minicells to a patient with a tumor, in a situation where the patient is exposed to an elevated level of INF-gamma, results in an anti-tumor response that is greatly improved compared to what is observed when IFN-gamma is not activated, e.g., when its level is below detection limits. This synergy between minicell-mediated anti-tumor activity and elevated IFN-gamma is apparent from the magnitude of increased tumor response. Without committing to any particular mechanism(s), the inventors contemplate that the approach described here exploits critical pathways in immune stimulation that are important in host anti-tumor responses. The bacterially derived minicells and IFN-gamma elicit different pathways in immune stimulation, which collectively is important in augmenting the anti-tumor response that the anti-neoplastic drug initiates upon intracellular delivery to tumor cells via the bispecific antibody-targeted minicells, in accordance with the present disclosure.

The inventors also discovered that blood vessels around tumor cells display a loss of integrity; that is, the vessels have large fenestrations and are "leaky," even in the blood brain barrier (BBB) environment. In contravention of conventional understanding, therefore, particles that are as large as minicells, i.e., much larger than the above-discussed consensus pore size limitations of the BBB, nevertheless are smaller than the fenestrations in the walls of the leaky blood vessel; hence, they can extravasate passively through these fenestrations and into the tumor microenvironment.

Upon entering the tumor microenvironment, minicells are able to trigger receptor-mediated internalization by the host tumor cells and to be taken up by them. Thus, a minicell that is packaged with an anti-neoplastic agent will release the agent into the cytoplasm of the tumor cell, killing it.

Although IFN-gamma has been suggested for use in tumor therapy, its clinical application has been limited to date, in no small part due to its high toxicity. The ability of IFN-gamma to stimulate immune response to tumor cells also has not seen much success. In the context of the present invention, therefore, the role played by IFN-gamma not only is advantageous but also is truly surprising.

In one of its aspects, therefore, the present disclosure provides a treatment for a tumor that entails administering to the patient with the tumor a composition comprised of a plurality of intact, bacterially derived minicells carrying an anti-neoplastic agent, while also administering to the patient an agent that increases his or her level of IFN-gamma. According to another aspect, killed bacterial cells can be used with or in lieu of minicells, since such cells likewise can be loaded with anti-cancer drug for release upon uptake into target tumor cells. See, e.g., published international application WO/2008/012695, the contents of which are incorporated here by reference.

The administration of a composition containing drug-loaded minicell and/or killed bacterial cell preferably is systemic, e.g., intravenous or intra-arterial. Further, the IFN-gamma or an agent inducing the expression of IFN-gamma can be administered by a route that is different, i.e., subcutaneous or intramuscular, but need not be. The minicell and/or killed bacterial cell therapeutic can be administered concomitantly with the IFN-gamma or at different times.

(A) Definitions

Unless defined otherwise, all technical and scientific terms used in this description have the same meaning as commonly understood by those skilled in the relevant art.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

"Cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this disclosure particularly apply to malignant, pre-metastatic, metastatic, and non-metastatic cells.

"Drug" refers to any physiologically or pharmacologically active substance that produces a local or systemic effect in animals, particularly mammals and humans.

"Individual," "subject," "host," and "patient," terms used interchangeably in this description, refer to any mammalian subject for whom diagnosis, treatment, or therapy is desired. The individual, subject, host, or patient can be a human or a non-human animal. Thus, suitable subjects can include but are not limited to non-human primates, cattle, horses, dogs, cats, guinea pigs, rabbits, rats, and mice.

The terms "treatment," "treating," "treat," and the like refer to obtaining a desired pharmacological and/or physiologic effect in a tumor patient. The effect can be prophylactic in terms of completely or partially preventing tumor or symptom thereof and/or can be therapeutic in terms of a partial or complete stabilization or cure for tumor and/or adverse effect attributable to the tumor. Treatment covers any treatment of a tumor in a mammal, particularly a human. A desired effect, in particular, is tumor response, which can be measured as reduction of tumor mass or inhibition of tumor mass increase. In addition to tumor response, an increase of overall survival, progress-free survival, or time to tumor recurrence or a reduction of adverse effect also can be used clinically as a desired treatment effect.

(B) Treatments

The present disclosure is reflected in and substantiated by experimental evidence that, in keeping with the inventors' discovery, bacterially derived and intact minicells or intact killed bacterial cells, when administered to a tumor patient along with an agent that increases the level of IFN-gamma, can achieve a therapeutic efficacy that is surprisingly greater than when the minicells or killed bacterial cells are administered alone.

(C) Anti-Neoplastic Agents

The phrase "anti-neoplastic agent" denotes a drug, whether chemical or biological, that prevents or inhibits the growth, development, maturation, or spread of neoplastic cells.

In the context of this disclosure, selecting an anti-neoplastic agent for treating a given tumor patient depends on several factors, in keeping with conventional medical practice. These factors include but are not limited to the patient's age, the stage of the tumor, and whatever previous therapy the patient may have received.

In accordance with the disclosure, a drug can be selected from one of the classes detailed below, for packaging into intact, bacterially derived minicells, which then are administered to treat a tumor. These drugs can also be synthetic analogs designed from drug design and discovery efforts.

Polyfunctional alkylating agents, exemplified by Cyclophosphamide (Cytoxan), Mechlorethamine, Melphalan (Alkeran), Chlorambucil (Leukeran), Thiopeta (Thioplex), Busulfan (Myleran).

Alkylating drugs, exemplified by Procarbazine (Matulane), Dacarbazine (DTIC), Altretamine (Hexalen), Clorambucil, Cisplatin (Platinol), Carboplatin, Ifosafamide, Oxaliplatin.

Antimetabolites, exemplified by Methotrexate (MTX), 6-Thiopurines (Mercaptopurine[6-MP], Thioguanine [6-TG]), Mercaptopurine (Purinethol), Thioguanine, Fludarabine phosphate, Cladribine: (Leustatin), Pentostatin, Flurouracil (5-FU), Cytarabine (ara-C), Azacitidine.

Plant alkaloids, terpenoids and topoisomerase inhibitors, exemplified by Vinblastine (Velban), Vincristine (Oncovin), Vindesine, Vinorelbine, Podophyllotoxins (etoposide {VP-16} and teniposide {VM-26}), Camptothecins (topotecan and irinotecan), Taxanes such as Paclitaxel (Taxol) and Docetaxel (Taxotere).

Antibiotics, exemplified by Doxorubicin (Adriamycin, Rubex, Doxil), Daunorubicin, Duocarmycin, Idarubicin, Dactinomycin (Cosmegen), Plicamycin (Mithramycin), Mitomycin: (Mutamycin), Bleomycin (Blenoxane).

Hormonal agents, exemplified by Estrogen and Androgen Inhibitors (Tamoxifen and Flutamide), Gonadotropin-Releasing Hormone Agonists (Leuprolide and Goserelin (Zoladex)), Aromatase Inhibitors (Aminoglutethimide and Anastrozole (Arimidex)).

Miscellaneous Anticancer Drugs, exemplified by Amsacrine, Asparaginase (El-spar), Hydroxyurea, Mitoxantrone (Novantrone), Mitotane (Lysodren), Maytansinoid, Retinoic acid Derivatives, Bone Marrow Growth Factors (sargramostim and filgrastim), Amifostine.

Agents disrupting folate metabolism, e.g., Pemetrexed.

DNA hypomethylating agents, e.g., Azacitidine, Decitabine.

Poly(adenosine diphosphate [ADP]-ribose) polymerase (PARP) pathway inhibitors, such as Iniparib, Olaparib, Veliparib.

PI3K/Akt/mTOR pathway inhibitors, e.g., Everolimus.

Histone deacetylase (HDAC) inhibitors, e.g., Vorinostat, Entinostat (SNDX-275), Mocetinostat (MGCD0103), Panobinostat (LBH589), Romidepsin, Valproic acid.

Cyclin-dependent kinase (CDK) inhibitors, e.g., Flavopiridol, Olomoucine, Roscovitine, Kenpaullone, AG-024322 (Pfizer), Fascaplysin, Ryuvidine, Purvalanol A, NU2058, BML-259, SU 9516, PD-0332991, P276-00.

Heat shock protein (HSP90) inhibitors, e.g., Geldanamycin, Tanespimycin, Alvespimycin, Radicicol, Deguelin, BIIB021.

Murine double minute 2 (MDM2) inhibitors, e.g., Cis-imidazoline, Benzodiazepinedione, Spiro-oxindoles, Isoquinolinone, Thiophene, 5-Deazaflavin, Tryptamine.

Anaplastic lymphoma kinase (ALK) inhibitors, e.g., Aminopyridine, Diaminopyrimidine, Pyridoisoquinoline, Pyrrolopyrazole, Indolocarbazole, Pyrrolopyrimidine, Dianilinopyrimidine.

Poly [ADPribose] polymerase (PARP) inhibitors, illustrated by Benzamide, Phthalazinone, Tricyclic indole, Benzimidazole, Indazole, Pyrrolocarbazole, Phthalazinone, Isoindolinone.

Active agents useable in the present disclosure are not limited to those drug classes or particular agents enumerated above. Different discovery platforms continue to yield new agents that are directed at unique molecular signatures of cancer cells; indeed, thousands of such chemical and biological drugs have been discovered, only some of which are listed here. Yet, the surprising capability of intact, bacterially derived minicells and killed bacterial cells to accommodate packaging of a diverse variety of active agents, hydrophilic or hydrophobic, means that essentially any such drug, when packaged in minicells, has the potential to treat a cancer, pursuant to the findings in the present disclosure.

Likewise illustrative of the class of anti-neoplastic agents are radionuclides, chemotherapy drugs, and functional nucleic acids, including but not limited to regulatory RNAs.

1. Radionuclides

A "radionuclide" is an atom with an unstable nucleus, i.e., one characterized by excess energy available to be imparted either to a newly created radiation particle within the nucleus or to an atomic electron. Therefore, a radionuclide undergoes radioactive decay, and emits gamma ray(s) and/or subatomic particles. Numerous radionuclides are known in the art, and a number of them are known to be suitable for medical use, such as yttrium-90, technetium-99m, iodine-123, iodine-124, iodine-125, iodine-131, rubidium-82, thallium-201, gallium-67, fluorine-18, xenon-133, and indium-111.

Radionuclides have found extensive use in nuclear medicine, particularly as beta-ray emitters for damaging tumor cells. Radionuclides are suitably employed, therefore, as anti-neoplastic agents in the present disclosure.

Radionuclides can be associated with intact, bacterially derived minicells by any known technique. Thus, a protein or other minicell-surface moiety (see below) can be labeled with a radionuclide, using a commercially available labeling means, such as use of Pierce™ Iodination reagent, a product of Pierce Biotechnology Inc. (Rockford, Ill.), detailed in Rice et al., *Semin. Nucl. Med.* 41, 265-282 (2011). Alternatively, radionuclides can be incorporated into proteins that are inside minicells.

In the latter situation, a minicell-producing bacterial strain is transformed with plasmid DNA encoding foreign protein. When minicells are formed during asymmetric cell division, several copies of the plasmid DNA segregates into the minicell cytoplasm. The resultant, recombinant minicells are incubated, in the presence of radiolabeled amino acids, under conditions such that foreign protein expressed inside the minicell, from the plasmid DNA, incorporates the radionuclide-carrying amino acids. Pursuant to the protocol of Clark-Curtiss and Curtiss, *Methods Enzymol.* 101: 347-362 (1983), for instance, recombinant minicells are incubated in minimal growth medium that contains $^{35}$S-methionine, whereby newly expressed, plasmid-encoded proteins incorporate the $^{35}$S-methionine. A similar approach can be used in order that recombinant minicells become packaged with other radiolabels, as desired.

Oligosaccharides on the minicell surface also can be radiolabeled using, for example, well-established protocols described by Fukuda, *Curr. Protocols Molec. Biol.* (Suppl. 26), 17.5.1-17.5.8 (1994). Illustrative of such oligosaccharides that are endemic to minicells is the O-polysaccharide component of the lipopolysaccharide (LPS) found on the surface of minicells derived from Gram-negative bacteria (see below).

A preferred methodology in this regard is to radiolabel a bispecific antibody that is used to target minicells to specific tumors. See section G, infra, and patent publication US 2007/0237744, the contents of which are incorporated herein by reference. That is, the bispecific antibody "coated" on a minicell exposes a significant amount of additional surface protein for radiolabeling. Accordingly, it is possible to achieve a higher specific activity of the radiolabel associated with the antibody-coated minicell. By contrast, the radiolabeling of non-coated minicells, i.e., when the radionuclide labels only endemic moieties, can result in weaker labeling (lower specific activity). In one embodiment, this weaker labeling is thought to occur because the outer membrane-associated proteins of minicells derived from Gram-negative bacteria are masked by LPS, which, as further discussed below, comprises long chains of O-polysaccharide covering the minicell surface.

For treating a tumor, a composition of the disclosure would be delivered in a dose or in multiple doses that in toto affords a level of in-tumor irradiation that is sufficient at least to reduce tumor mass, if not eliminate the tumor altogether. The progress of treatment can be monitored along this line, on a case-by-case basis. In general terms, however, the amount of radioactivity packaged in the composition typically will be on the order of about 30 to 50 Gy, although the invention also contemplates a higher amount of radioactivity, say, about 50 to 200 Gy, which gives an overall range between about 30 Gy and about 200 Gy.

In some instances the amount of radioactivity packaged in the composition can be even lower than mentioned above, given the highly efficient and specific delivery of the minicell-bourne radionuclides to a tumor. Accordingly, in one aspect the composition contains from about 20 to 40 Gy, or about 10 to 30 Gy, or about 1 to about 20 Gy, or less than 10 Gy.

2. Chemotherapy Drugs

An anti-neoplastic agent employed in the present disclosure also can be a chemotherapy drug. In this description, "chemotherapeutic drug," "chemotherapeutic agent," and "chemotherapy" are employed interchangeably to connote a drug that has the ability to kill or disrupt a neoplastic cell. A chemotherapeutic agent can be a small molecule drug or a biologic drug, as further detailed below.

The "small molecule drug" subcategory encompasses compounds characterized by having (i) an effect on a biological process and (ii) a low molecular weight as compared to a protein or polymeric macromolecule. Small molecule drugs typically are about 800 Daltons or less, with a lower limit of about 150 Daltons, as illustrated by Temodar® (temozolomide), at about 194 Daltons, which is used to treat gliaoblastoma multiforme and other types of brain cancer. In this context "about" indicates that the qualified molecular-weight value is subject to variances in measurement precision and to experimental error on the order of several Daltons or tens of Daltons. Thus, a small molecule drug can have a molecular weight of about 900 Daltons or less, about 800 or less, about 700 or less, about 600 or less, about 500 or less, or about 400 Daltons or less, e.g., in the range of about 150 to about 400 Daltons. More specifically, a small molecule drug can have a molecular weight of about 400 Daltons or more, about 450 Daltons or more, about 500 Daltons or more, about 550 Daltons or more, about 600 Daltons or more, about 650 Daltons or more, about 700 Daltons or more, or about 750 Daltons or more. In another embodiment, the small molecule drug packaged into the minicells has a molecular weight between about 400 and about 900 Daltons, between about 450 and about 900 Daltons, between about 450 and about 850 Daltons, between about 450 and about 800 Daltons, between about 500 and about 800 Daltons, or between about 550 and about 750 Daltons.

Specifically, suitable small molecule drugs include but are not limited to nitrogen mustards, nitrosorueas, ethyleneimine, alkane sulfonates, tetrazine, platinum compounds, pyrimidine analogs, purine analogs, anti-metabolites, folate analogs, anthracyclines, taxanes, vinca alkaloids, and topoisomerase inhibitors, inter alia. Accordingly, a small molecule drug for use in the present invention can be selected from among any of the following, inter alia: enediynes, such as dynemicin A, unicalamycin, calicheamicin γ1 and calicheamicin θ1; meayamicin, a synthetic analog of FR901464; benzosuberene derivatives as described, for example, by Tanpure et al., *Bioorg. Med. Chem.* 21: 8019-32 (2013); auristatins, such as auristatin E, mono-methyl auristatin E (MMAE), and auristatin F, which are synthetic analogs of dolastatin; duocarmysins such as duocarmycin SA and CC-1065; maytansine and its derivatives (maytansinoids), such as DM1 and DM4; irinotecan (Camptosar®) and other topoisomerase inhibitors, such as topotecan, etoposide, mitoxantrone and teniposide; and yatakemycin, the synthesis of which is detailed by Okano et al., *J. Am. Chem. Soc.* 128: 7136-37 (2006).

More particularly, any one or more or all of the specific small molecule drugs detailed in this paragraph are illustrative of those suitable for use in this invention: actinomycin-D, alkeran, ara-C, anastrozole, BiCNU, bicalutamide, bisantrene, bleomycin, busulfan, capecitabine (Xeloda®), carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, and VP-16.

For purposes of this description a "biologic drug" is defined, by contrast, to denote any biologically active macromolecule that can be created by a biological process, exclusive of "functional nucleic acids," discussed below, and polypeptides that by size qualify as small molecule drugs, as defined above. The "biologic drug" subcategory thus is exclusive of and does not overlap with the small molecule drug and functional nucleic acid subcategories. Illustrative of biologic drugs are therapeutic proteins and antibodies, whether natural or recombinant or synthetically made, e.g., using the tools of medicinal chemistry and drug design.

Certain molecules that are designed for chemotherapeutic purposes nevertheless fail during pre-clinical or clinical trials due to unacceptable toxicity or other safety concerns. The present inventors have shown that packaging a chemotherapy drug in a minicell, followed by systemic delivery to a tumor patient, results in delivery of the drug to tumor cells. Further, even after the tumor cells are broken up and the drug-containing cytoplasm is released to the nearby normal tissue, the result is not toxicity to normal tissue. This is because the drug already is bound to the tumor cellular structures, such as DNA, and can no longer attack normal cells. Accordingly, the present invention is particularly useful for delivery of highly toxic chemotherapy drugs to a tumor patient.

The phrases "highly toxic chemotherapy drug" and "supertoxic chemotherapy drug" in this description refer to chemotherapy drugs that have a relatively low lethal dose to normal cells as compared to their effective dose for cancer cells. Thus, in one aspect a highly toxic chemotherapy drug has a median lethal dose ($LD_{50}$) that is lower than its median effective dose ($ED_{50}$) for a targeted cancer such as (1) a cancer type for which the drug is designed, (2) the first cancer type in which a pre-clinical or clinical trial is run for that drug, or (3) the cancer type in which the drug shows the highest efficacy among all tested cancers. For instance, a highly toxic chemotherapy drug can have an $LD_{50}$ that is lower than about 500%, 400%, 300%, 250%, 200%, 150%, 120%, or 100% of the $ED_{50}$ of the drug for a targeted cancer. In another aspect, a highly toxic chemotherapy drug has a maximum sub-lethal dose (i.e., the highest dose that does not cause serious or irreversible toxicity) that is lower than its minimum effective dose for a targeted cancer, e.g., about 500%, 400%, 300%, 250%, 200%, 150%, 120%, 100%, 90%, 80%, 70%, 60% or 50% of the minimum effective dose.

According to one embodiment of the present description, therefore, a tumor in a subject is treated by a method comprising administering systemically a therapeutically effective amount of a composition comprised of a plurality of intact, bacterially derived minicells, each of which encompasses a highly toxic chemotherapy drug. Maytansinoids and duocarmycins, discussed below, are representative of the class of supertoxic chemotherapy drugs thus employed.

Suitable cancer chemotherapy drugs in the context include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors, and hormonal agents, inter alia.

Chemotherapy drugs that are illustrative of the small molecule drug subcategory are actinomycin-D, alkeran, ara-C, anastrozole, BiCNU, bicalutamide, bleomycin, busulfan, capecitabine (Xeloda®), carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, and VP-16.

Maytansinoids (molecular weight: ~738 Daltons) are a group of chemical derivatives of maytansine, having potent cytotoxicity. Although considered unsafe for human patient use, due to toxicity concerns, maytansinoids are suitable for delivery to tumor patients via minicells, pursuant to the present invention.

Duocarmycins (molecular weight: ~588 Daltons) are a series of related natural products, first isolated from *Streptomyces* bacteria. They also have potent cytotoxicity but are considered as unsafe for human use. Like maytansinoids, duocarmycins are suitable chemotherapy drugs for use in the invention.

Likewise illustrative are compounds in the class of morpholinyl anthracycline derivatives described in international patent application WO1998/002446. Among such derivatives are nemorubicin (3'-deamino-3'-[2(S)-methoxy-4-morpholinyl]doxorubicin), a/k/a MMDX, and its major metabolite PNU-159682 (3'-deamino-3"-4'-anhydro-[2"(S)-methoxy-3"(R)-hydroxy-4"-morpholinyl] doxorubicin), the structural formula of which is shown below, as well as these four other such derivatives described in U.S. Pat. No. 8,470,984, the contents of which are incorporated here by reference: 3'-deamino-3"-4'-anhydro-[2"(S)-methoxy-3" (R)-hydroxy-4"-morpholinyl] idarubicin; 3'-deamino-3"-4'-anhydro-[2"(S)-methoxy-3"(R)-hydroxy-4"-morpholinyl] daunorubicin; 3'-deamino-3"-4'-anhydro-[2"(S)-methoxy-3"

(R)-hydroxy-4"-morpholinyl]-caminomycin; and 3'-deamino-3"-4'-anhydro-[2"(S)-ethoxy-3"(R)-hydroxy-4"-morpholinyl]d-oxorubicin.

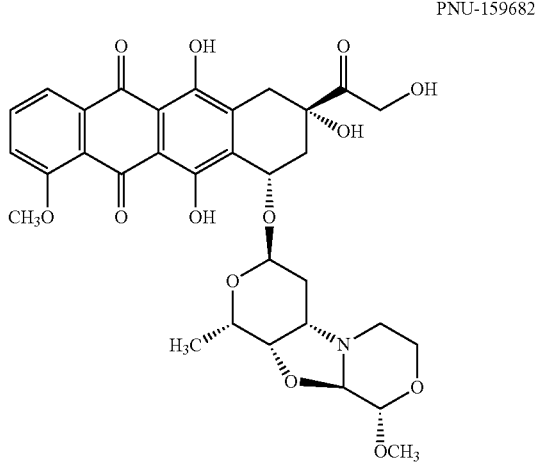

PNU-159682

A pharmaceutically acceptable acid addition salt of any of the aforementioned derivatives also is a member, pursuant to the invention, of this group of autofluorescent morpholinyl anthracycline derivatives.

The subcategory of biologic chemotherapy drugs includes, without limitation, asparaginase, AIN-457, bapineuzumab, belimumab, brentuximab, briakinumab, canakinumab, cetuximab, dalotuzumab, denosumab, epratuzumab, estafenatox, farletuzumab, figitumumab, galiximab, gemtuzumab, girentuximab (WX-G250), ibritumomab, inotuzumab, ipilimumab, mepolizumab, muromonab-CD3, naptumomab, necitumumab, nimotuzumab, ocrelizumab, ofatumumab, otelixizumab, ozogamicin, pagibaximab, panitumumab, pertuzumab, ramucirumab, reslizumab, rituximab, REGN88, solanezumab, tanezumab, teplizumab, tiuxetan, tositumomab, trastuzumab (Herceptin®), tremelimumab, vedolizumab, zalutumumab, and zanolimumab.

The composition can contain at most about 1 mg of the chemotherapeutic drug. Alternatively, the amount of the chemotherapeutic drug can be at most about 750 µg, 500 µg, 250 µg, 100 µg, 50 µg, 10 µg, 5 µg, 1 µg, 0.5 µg, or 0.1 µg. In another aspect, the composition contains a chemotherapeutic drug having an amount of less than about 1/1,000, or alternatively less than about 1/2,000, 1/5,000, 1/10,000, 1/20,000, 1/50,000, 1/100,000, 1/200,000 or 1/500,000 of the therapeutically effective amount of the drug when used without being packaged to into minicells. Pursuant to yet another aspect of the disclosure, the composition can contain at least about 1 nmol of the chemotherapeutic drug. Accordingly, the disclosure also encompasses embodiments where the amount of the chemotherapeutic drug is at least about 2 nmol, about 3 nmol, about 4 nmol, about 5 nmol, about 10 nmol, about 20 nmol, about 50 nmol, about 100 nmol, and about 800 nmol, respectively.

3. Functional Nucleic Acids

"Functional nucleic acid" refers to a nucleic acid molecule that, upon introduction into a host cell, specifically interferes with expression of a protein. With respect to treating a tumor, in accordance with the disclosure, it is preferable that a functional nucleic acid payload delivered to tumor cells via intact, bacterially derived minicells inhibits a gene that promotes tumor cell proliferation, angiogenesis or resistance to chemotherapy and/or that inhibits apoptosis or cell-cycle arrest; i.e., a "tumor-promoting gene."

It is generally the case that functional nucleic acid molecules used in this disclosure have the capacity to reduce expression of a protein by interacting with a transcript for a protein. This category of minicell payload for the disclosure includes regulatory RNAs, such as siRNA, shRNA, short RNAs (typically less than 400 bases in length), micro-RNAs (miRNAs), ribozymes and decoy RNA, antisense nucleic acids, and LincRNA, inter alia. In this regard, "ribozyme" refers to an RNA molecule having an enzymatic activity that can repeatedly cleave other RNA molecules in a nucleotide base sequence-specific manner. "Antisense oligonucleotide" denotes a nucleic acid molecule that is complementary to a portion of a particular gene transcript, such that the molecule can hybridize to the transcript and block its translation. An antisense oligonucleotide can comprise RNA or DNA. The "LincRNA" or "long intergenic non-coding RNA" rubric encompasses non-protein coding transcripts longer than 200 nucleotides. LincRNAs can regulate the transcription, splicing, and/or translation of genes, as discussed by Khalil et al., Proc Nat'l Acad. USA 106: 11667-72 (2009), for instance.

Each of the types of regulatory RNA can be the source of functional nucleic acid molecule that inhibits a tumor-promoting gene as described above and, hence, that is suitable for use according to the present disclosure. Thus, in one preferred embodiment of the disclosure the intact minicells carry siRNA molecules mediating a post-transcriptional, gene-silencing RNA interference (RNAi) mechanism, which can be exploited to target tumor-promoting genes. For example, see MacDiarmid et al., Nature Biotech. 27: 645-51 (2009) (antibody-presenting minicells deliver, with chemotherapy drug, siRNAs that counter developing resistance to drug), and Oh and Park, Advanced Drug Delivery Rev. 61: 850-62 (2009) (delivery of therapeutic siRNAs to treat breast, ovarian, cervical, liver, lung and prostate cancer, respectively).

As noted, "siRNA" generally refers to double-stranded RNA molecules from about 10 to about 30 nucleotides long that are named for their ability specifically to interfere with protein expression. Preferably, siRNA molecules are 12-28 nucleotides long, more preferably 15-25 nucleotides long, still more preferably 19-23 nucleotides long and most preferably 21-23 nucleotides long. Therefore, siRNA molecules can be 12, 13, 14, 15, 16, 17, 18, 19, 20, 21, 22, 23, 24, 25, 26, 27 28 or 29 nucleotides in length.

The length of one strand designates the length of an siRNA molecule. For instance, an siRNA that is described as 21 ribonucleotides long (a 21-mer) could comprise two opposing strands of RNA that anneal for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

Tools to assist the design of siRNA specifically and regulatory RNA generally are readily available. For instance, a computer-based siRNA design tool is available on the internet at www.dharmacon.com.

In another preferred embodiment, the intact minicells of the present disclosure carry miRNAs, which, like siRNA, are capable of mediating a post-transcriptional, gene-silencing RNA interference (RNAi) mechanism. Also like siRNA, the gene-silencing effect mediated by miRNA can be exploited to target tumor-promoting genes. For example, see Kota et al., *Cell* 137: 1005-17 (2009) (delivery of a miRNA via transfection resulted in inhibition of cancer cell proliferation, tumor-specific apoptosis and dramatic protection from disease progression without toxicity in murine liver cancer model), and Takeshita, et al., *Molec. Ther.* 18: 181-87 (2010) (delivery of synthetic miRNA via transient transfection inhibited growth of metastatic prostate tumor cells on bone tissues).

Although both mediate RNA interference, miRNA and siRNA have noted differences. In this regard, "miRNA" generally refers to a class of 17- to 27-nucleotide single-stranded RNA molecules (instead of double-stranded as in the case of siRNA). Therefore, miRNA molecules can be 17, 18, 19, 20, 21, 22, 23, 24, 25, 26, 27 nucleotides in length. Preferably, miRNA molecules are 21-25 nucleotide long.

Another difference between miRNAs and siRNAs is that the former generally do not fully complement the mRNA target. On the other hand, siRNA must be completely complementary to the mRNA target. Consequently, siRNA generally results in silencing of a single, specific target, while miRNA is promiscuous.

Additionally, although both are assembled into RISC (RNA-induced silencing complex), siRNA and miRNA differ in their respective initial processing before RISC assembly. These differences are described in detail in Chu et al., *PLoS Biology* 4: 1122-36 (2006), and Gregory et al., *Methods in Molecular Biology* 342: 33-47 (2006).

A number of databases serve as miRNA depositories. For example, see miRBase (www.mirbase.org) and tarbase (http://diana.cslab.ece.ntua.gr/DianaToolsNew/index.php?r=tarbase/index). In conventional usage, miRNAs typically are named with the prefix "-mir," combined with a sequential number. For instance, a new miRNA discovered after mouse mir-352 will be named mouse "mir-353."

Again, tools to assist the design of regulatory RNA including miRNA are readily available. In this regard, a computer-based miRNA design tool is available on the internet at wmd2.weigelworld.org/cgi-bin/mirnatools.pl.

As noted above, a functional nucleic acid employed in the disclosure can inhibit a gene that promotes tumor cell proliferation, angiogenesis or resistance to chemotherapy. The inhibited gene also can itself inhibit apoptosis or cell cycle arrest. Examples of genes that can be targeted by a functional nucleic acid are provided below.

Functional nucleic acids of the disclosure preferably target the gene or transcript of a protein that promotes drug resistance, inhibits apoptosis or promotes a neoplastic phenotype. Successful application of functional nucleic acid strategies in these contexts have been achieved in the art, but without the benefits of minicell vectors. See, e.g., Sioud, *Trends Pharmacol. Sci.* 25: 22-8 (2004), Caplen, *Expert Opin. Biol. Ther.* 3: 575-86 (2003), Nieth et al., *FEBS Lett.* 545: 144-50 (2003), Caplen and Mousses, *Ann. NY Acad. Sci.* 1002: 56-62 (2003), Duxbury et al., *Ann. Surg.* 240: 667-74 (2004), Yague et al., *Gene Ther.* 11: 1170-74 (2004), and Duan et al., *Mol. Cancer Ther.* 3: 833-8 (2004).

Proteins that contribute to drug resistance constitute preferred targets of functional nucleic acids. The proteins may contribute to acquired drug resistance or intrinsic drug resistance. When diseased cells, such as tumor cells, initially respond to drugs, but become refractory on subsequent treatment cycles, the resistant phenotype is acquired. Useful targets involved in acquired drug resistance include ATP binding cassette transporters such as P-glycoprotein (P-gp, P-170, PGY1, MDR1, ABCB1, MDR-associated protein, Multidrug resistance protein 1), MDR-2 and MDR-3. MRP2 (multi-drug resistance associated protein), BCR-ABL (breakpoint cluster region—Abelson protooncogene), a STI-571 resistance-associated protein, lung resistance-related protein, cyclooxygenase-2, nuclear factor kappa, XRCC1 (X-ray cross-complementing group 1), ERCC1 (excision cross-complementing gene), GSTP1 (glutathione S-transferase), mutant β-tubulin, and growth factors such as IL-6 are additional targets involved in acquired drug resistance.

Particularly useful targets that contribute to drug resistance include ATP binding cassette transporters such as P-glycoprotein, MDR-2, MDR-3, BCRP, APT11a, and LRP.

Useful targets also include proteins that promote apoptosis resistance. These include Bcl-2 (B cell leukemia/lymphoma), Bcl-$X_L$, Al/Bfl 1, focal adhesion kinase, dihydrodiol dehydrogenase, and p53 mutant protein.

Useful targets further include oncogenic and mutant tumor suppressor proteins. Illustrative of these are β-Catenin, PKC-α (protein kinase C), C-RAF, K-Ras (V 12), DP97 Dead box RNA helicase, DNMT1 (DNA methyltransferase 1), FLIP (Flice-like inhibitory protein), C-Sfc, 53BPI, Polycomb group protein EZH2 (Enhancer of zeste homologue), ErbB1, HPV-16 E5 and E7 (human papillomavirus early 5 and early 7), Fortilin & MCI1P (Myeloid cell leukemia 1 protein), DIP13α (DDC interacting protein 13a), MBD2 (Methyl CpG binding domain), p21, KLF4 (Kruppel-like factor 4), tpt/TCTP (Translational controlled tumor protein), SPK1 and SPK2 (Sphingosine kinase), P300, PLK1 (Polo-like kinase-1), Trp53, Ras, ErbB1, VEGF (Vascular endothelial growth factor), BAG-1 (BCL2-associated athanogene 1), MRP2, BCR-ABL, STI-571 resistance-associated protein, lung resistance-related protein, cyclooxygenase-2, nuclear factor kappa, XRCC1, ERCC1, GSTP1, mutant β-tubulin, and growth factors.

Also useful as targets are global regulatory elements exemplified by the cytoplasmic polyadenylation element binding proteins (CEPBs). For instance, CEPB4 is overexpressed in glioblastoma and pancreatic cancers, where the protein activates hundreds of genes associated with tumor growth, and it is not detected in healthy cells (Oritz-Zapater et al., *Nature Medicine*, doi: 10.1038/nm.2540 (published on-line Dec. 4, 2011)). In accordance with the present description, therefore, treatment of a glioblastoma could be effected via administration of a composition containing intact, bacterially derived minicells that encompass an agent that counters overexpression of CEPB4, such as an siRNA or other functional nucleic acid molecule that disrupts CEPB4 expression by the tumor cells.

Further useful functional nucleic acids are those that are involved in DNA replication and repair. Examples include ribonucleotide reductase (RR), which is a potential therapeutic target for cancer because it catalyzes the conversion of ribonucleoside 5'-diphosphates into their corresponding 2'-deoxyribonucleoside 5'-triphosphates that are necessary for DNA replication and repair. See D'Angiolella et al., *Cell:* 149:1023-34 (2012). Human RR comprises two subunits, RRM1 and RRM2, and functional nucleic acids that target both subunits are useful in the present invention. A further example of useful functional nucleic acids include replication protein A (RPA), a trimeric complex composed of 70-kDa (RPA1), 32-kDa (RPA2), and 14-kDa (RPA3) subunits, which is essential for DNA replication in all organisms. See Iftode et al., *Crit. Rev. Biochem. Mol. Biol.* 34: 141-80 (1999).

(D) Tumors

The compositions and methods of the present disclosure are useful in treating a variety of tumor types, not limited to a particular kind. This is because the minicells or killed bacterial cells can package different anti-neoplastic agents and, in particular when attached with a bispecific ligand specific to different tumor cells, can target cells of different tumor types. In addition, the ability of minicells or killed bacterial cells, in combination with IFN-gamma, are expected to be able to stimulate immune response to any tumor cells.

In accordance with one embodiment of the disclosure, the present compositions and methods are used in treating one or more cancers selected from adrenal cancer, anal cancer, aplastic anemia, bile duct cancer, bladder cancer, bone cancer, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, leukemia—acute lymphocytic (ALL) in adults, leukemia—acute myeloid (AML), leukemia—chronic lymphocytic (CLL), leukemia—chronic myeloid (cml), leukemia—chronic myelomonocytic (CMML), leukemia in children, liver cancer, lung cancer, lung cancer—non-small cell, lung cancer—small cell, lung carcinoid tumor, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer, skin cancer—basal and squamous cell, skin cancer—melanoma, small intestine cancer, stomach cancer, testicular cancer, thymus cancer, thyroid cancer, uterine sarcoma, vaginal cancer, vulvar cancer, Waldenstrom macroglobulinemia, and Wilms tumor.

In one embodiment, the compositions and methods are suitable for treating brain tumor. There are more than 120 types of brain tumors. Most medical institutions use the World Health Organization (WHO) classification system to identify brain tumors. The WHO classifies brain tumors by cell origin and how the cells behave, from the least aggressive (benign) to the most aggressive (malignant). Some tumor types are assigned a grade, ranging from Grade I (least malignant) to Grade IV (most malignant), which signifies the rate of growth. There are variations in grading systems, depending on the tumor type. The classification and grade of an individual tumor help predict its likely behavior. The most frequently diagnosed types include acoustic neuroma, astrocytoma (including Grade I—pilocytic astrocytoma, Grade II—low-grade astrocytoma, Grade III—anaplastic astrocytoma, and Grade IV—glioblastoma (GBM)), chordoma, CNS lymphoma, craniopharyngioma, other gliomas (brain stem glioma, ependymoma, mixed glioma, optic nerve glioma and subependymoma), medulloblastoma, meningioma, metastatic brain tumors, oligodendroglioma, pituitary tumors, primitive neuroectodermal (PNET), other brain-related conditions, and schwannoma.

Among children, these brain tumor types are more common: brain stem glioma, craniopharyngioma, ependymoma, juvenile pilocytic astrocytoma (JPA), medulloblastoma, optic nerve glioma, pineal tumor, primitive neuroectodermal tumors (PNET), and rhabdoid tumor.

(E) Minicells and Killed Bacterial Cells

"Minicell" refers to a derivative of a bacterial cell that is lacking in chromosomes ("chromosome-free") and is engendered by a disturbance in the coordination, during binary fission, of cell division with DNA segregation. Minicells are distinct from other small vesicles, such as so-called "membrane blebs" (~0.2 µm or less in size), which are generated and released spontaneously in certain situations but which are not due to specific genetic rearrangements or episomal gene expression. By the same token, intact minicells are distinct from bacterial ghosts, which are not generated due to specific genetic rearrangements or episomal gene expression. Bacterially derived minicells employed in this disclosure are fully intact and thus are distinguished from other chromosome-free forms of bacterial cellular derivatives characterized by an outer or defining membrane that is disrupted or degraded, even removed. See U.S. Pat. No. 7,183,105 at column 111, lines 54 et seq. The intact membrane that characterizes the minicells of the present disclosure allows retention of the therapeutic payload within the minicell until the payload is released, post-uptake, within a tumor cell.

The minicell employed in this disclosure can be prepared from bacterial cells, such as *E. coli* and *S. typhymurium*. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an chromosome-less minicell. See de Boer et al., *J. Bacteriol.* 174(1): 63-70 (1992); Raskin & de Boer, *J. Bacteriol.* 181: 6419-6424 (1999); Hu & Lutkenhaus, *Mol. Microbio.* 34(1): 82-90 (1999); Harry, *Mol. Microbiol.* 40(4): 795-803 (2001).

In addition to min operon mutations, chromosome-less minicells also are generated following a range of other genetic rearrangements or mutations that affect septum formation, for example, in the divIVB1 in *B. subtilis*. See Reeve and Cornett, *J. Virol.* 15: 1308-16 (1975). Minicells also can be formed following a perturbation in the levels of gene expression of proteins involved in cell division/chromosome segregation. For instance, over-expression of minE leads to polar division and production of minicells. Similarly, chromosome-less minicells can result from defects in chromosome segregation, e.g., the smc mutation in *Bacillus subtilis* (Britton et al., *Genes Dev.* 12: 1254-9 (1998)), the spoOJ deletion in *B. subtilis* (Ireton et al., *J. Bacteriol.* 176: 5320-29 (1994)), the mukB mutation in *E. coli* (Hiraga et al., *J. Bacteriol.* 171: 1496-1505 (1989)), and the parC mutation in *E. coli* (Stewart and D'Ari, *J. Bacteriol.* 174: 4513-6 (1992)). Further, CafA can enhance the rate of cell division and/or inhibit chromosome partitioning after replication (Okada et al., *J. Bacteriol.* 176: 917-22 (1994)), resulting in formation of chained cells and chromosome-less minicells.

Accordingly, minicells can be prepared for the present disclosure from any bacterial cell, be it of Gram-positive or Gram-negative origin due to the conserved nature of bacterial cell division in these bacteria. Furthermore, the minicells used in the disclosure should possess intact cell walls (i.e., are "intact minicells"), as noted above, and should be distinguished over and separated from other small vesicles, such as membrane blebs, which are not attributable to specific genetic rearrangements or episomal gene expression.

In a given embodiment, the parental (source) bacteria for the minicells can be Gram positive, or they can be Gram negative, as mentioned. In one aspect, therefore, the parental bacteria are one or more selected from Terra-/Glidobacteria (BV1), Proteobacteria (BV2), BV4 including Spirochaetes, Sphingobacteria, and Planctobacteria. Pursuant to another aspect, the bacteria are one or more selected from Firmicutes (BV3) such as Bacilli, Clostridia or Tenericutes/Mollicutes, or Actinobacteria (BV5) such as Actinomycetales or Bifidobacteriales.

Pursuant to the invention, killed bacterial cells are non-living prokaryotic cells of bacteria, cyanobateria, eubacteria and archaebacteria, as defined in the 2nd edition of BERGEY'S MANUAL OF SYSTEMATIC BIOLOGY. Such cells are deemed to be "intact" if they possess an intact cell wall and/or cell membrane and contain genetic material (nucleic acid) that is endogenous to the bacterial species. Methods of preparing killed bacterial cells are described, for instance, in U.S. patent application publication No. 2008/0038296, the contents of which are incorporated here by reference.

In yet a further aspect, the bacteria are one or more selected from Eobacteria (Chloroflexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/Verrucomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycineae, Actinomycetaceae, Corynebacterineae, Nocardiaceae, Corynebacteriaceae, Frankineae, Frankiaceae, Micrococcineae, Brevibacteriaceae, and Bifidobacteriaceae.

For pharmaceutical use, a composition of the disclosure should comprise minicells or killed bacterial cells that are isolated as thoroughly as possible from immunogenic components and other toxic contaminants. Methodology for purifying bacterially derived minicells to remove free endotoxin and parent bacterial cells are described in WO 2004/113507, which is incorporated by reference here in its entirety. Briefly, the purification process achieves removal of (a) smaller vesicles, such as membrane blebs, which are generally smaller than 0.2 µm in size, (b) free endotoxins released from cell membranes, and (c) parental bacteria, whether live or dead, and their debris, which are sources of free endotoxins, too. Such removal can be implemented with, inter alia, a 0.2 µm filter to remove smaller vesicles and cell debris, a 0.45 µm filter to remove parental cells following induction of the parental cells to form filaments, antibiotics to kill live bacterial cells, and antibodies against free endotoxins.

Underlying the purification procedure is a discovery by the present inventors that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. On the other hand, dynamic light scattering can measure the same minicells to be approximately 500 nm±50 nm in size. Also, drug-packaged, ligand-targeted minicells can be measured, again using dynamic light scattering, to be approximately 400 nm to 600 nm±50 nm.

This scatter of size values is readily accommodated in practice, e.g., for purposes of isolating minicells from immunogenic components and other toxic contaminants, as described above. That is, an intact, bacterially derived minicell is characterized by cytoplasm surrounded by a rigid membrane, which gives the minicell a rigid, spherical structure. This structure is evident in transmission-electron micrographs, in which minicell diameter is measured, across the minicell, between the outer limits of the rigid membrane. This measurement provides the above-mentioned size value of 400 nm±50 nm.

Another structural element of a killed bacterial cells or a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the O-polysaccharide component, dynamic light scattering can provide a value for minicell size of about 500 nm to about 600 nm, as noted above. Nevertheless, minicells from Gram-negative and Gram-positive bacteria alike readily pass through a 0.45 µm filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure can contain less than about 350 EU free endotoxin. Illustrative in this regard are levels of free endotoxin of about 250 EU, about 200 EU, about 150 EU, about 100 EU, about 90 EU, about 80 EU, about 70 EU, about 60 EU, about 50 EU, about 40 EU, about 30 EU, about 20 EU, about 15 EU, about 10 EU, about 9 EU, about 8 EU, about 7 EU, about 6 EU, about 5 EU, about 4 EU, about 3 EU, about 2 EU, about 1 EU, about 0.9 EU, about 0.8 EU, about 0.7 EU, about 0.6 EU, about 0.5 EU, about 0.4 EU, about 0.3 EU, about 0.2 EU, about 0.1 EU, about 0.05 EU, and about 0.01 EU, respectively.

A composition of the disclosure also can contain at least about $10^9$ minicells or killed bacterial cells, e.g., at least about $1 \times 10^9$, at least about $2 \times 10^9$, or at least about $5 \times 10^9$. In some embodiments, the composition contains no more than about $10^{11}$ minicells or killed bacterial cells, e.g., no more than about $1 \times 10^{11}$ or no more than about $9 \times 10^{10}$, or no more than about $8 \times 10^{10}$ (F) Packaging an Anti-Neoplastic Agent into Minicells or Killed Bacterial Cells Anti-neoplastic agents, such as proteins and functional nucleic acids, that can be encoded by a nucleic acid, can be introduced into minicells by transforming into the parental bacterial cell a vector, such as a plasmid, that encodes the anti-neoplastic agent. When a minicell is formed from the parental bacterial cell, the minicell retains certain copies of the plasmid and/or the expression product, the anti-neoplastic agent. More details of packaging an expression product into a minicell is provided in WO 03/033519, the contents of which are incorporated into the present disclosure in its entirety by reference.

Data presented in WO 03/033519 demonstrated, for example, that recombinant minicells carrying mammalian gene expression plasmids can be delivered to phagocytic cells and to non-phagocytic cells. The application also described the genetic transformation of minicell-producing parent bacterial strains with heterologous nucleic acids carried on episomally-replicating plasmid DNAs. Upon separation of parent bacteria and minicells, some of the episomal DNA segregated into the minicells. The resulting recombinant minicells were readily engulfed by mammalian phagocytic cells and became degraded within intracellular phagolysosomes. Moreover, some of the recombinant DNA escaped the phagolysosomal membrane and was transported to the mammalian cell nucleus, where the recombinant genes were expressed.

Nucleic acids also can be packaged into minicells directly. Thus, a nucleic acid can be packaged directly into intact minicells by co-incubating a plurality of intact minicells with the nucleic acid in a buffer. The buffer composition can be varied, as a function of conditions well known in this field, in order to optimize the loading of the nucleic acid in the intact minicells. The buffer also may be varied in dependence on the nucleotide sequence and the length of the nucleic acid to be loaded in the minicells. Exemplary buffer suitable for loading includes, but is not limited to, phosphate buffered saline (PBS). Once packaged, the nucleic acid remains inside the minicell and is protected from degradation. Prolonged incubation studies with siRNA-packaged minicells incubated in sterile saline have shown, for example, no leakage of siRNAs.

In other embodiments, multiple nucleic acids directed to different mRNA targets can be packaged in the same minicell. Such an approach can be used to combat drug resistance and apoptosis resistance. For instance, cancer patients routinely exhibit resistance to chemotherapeutic drugs. Such resistance can be mediated by over-expression of genes such as multi-drug resistance (MDR) pumps and anti-apoptotic genes, among others. To combat this resistance, minicells can be packaged with therapeutically significant concentrations of functional nucleic acid to MDR-associated genes and administered to a patient before chemotherapy. Furthermore, packaging into the same minicell multiple functional nucleic acid directed to different mRNA targets can enhance therapeutic success since most molecular targets are subject to mutations and have multiple alleles. More details of directly packaging a nucleic acid into a minicell is provided in WO 2009/027830, the contents of which are incorporated into the present disclosure in its entirety by reference.

Small molecule drugs, whether hydrophilic or hydrophobic, can be packaged in minicells by creating a concentration gradient of the drug between an extracellular medium containing minicells and the minicell cytoplasm. When the extracellular medium contains a higher drug concentration than the minicell cytoplasm, the drug naturally moves down this concentration gradient, into the minicell cytoplasm. When the concentration gradient is reversed, however, the drug does not move out of the minicells. More details of the drug loading process and its surprising nature are found, for instance, in U.S. Patent Application Publication No. 2008/0051469.

To load minicells with drugs that normally are not water soluble, the drugs initially can be dissolved in an appropriate solvent. For example, paclitaxel can be dissolved in a 1:1 blend of ethanol and Cremophor EL® (polyethoxylated castor oil), followed by a dilution in PBS to achieve a solution of paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm or the membrane of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm.

It is demonstrated the loading into minicells of a diversity of representative small molecule drugs, illustrating different sizes and chemical properties: Doxorubicin, paclitaxel, fluoro-paclitaxel, cisplatin, vinblastine, monsatrol, thymidylate synthase (TS) inhibitor OSI-7904, irinotecan, 5-fluorouracil, gemcitabine, and carboplatin. Across the board, moreover, the resultant, small molecule drug-packaged minicells show significant anti-tumor efficacy, in vitro and in vivo. These data presented here therefore demonstrate the effectiveness and versatility of the minicell loading methodology.

(G) Directing Minicells or Killed Bacterial Cells to Specific Mammalian Cells

Pursuant to a further aspect of this disclosure, the minicells or killed bacterial cells of a composition, as described above, are directed to a target mammalian tumor cell via a ligand. In some embodiments the ligand is "bispecific." That is, the ligand displays a specificity for both minicell and mammalian (tumor) cell components, such that it causes a given vesicle to bind to the target cell, whereby the latter engulfs the former. Use of bispecific ligands to target a minicell to a tumor cell is further described in WO 05/056749 and WO 05/079854, and use of bispecific ligands to target a killed bacterial cell to a tumor cell is further described in U.S. Pat. No. 8,591,862, the respective contents of which are incorporated here by reference in its entirety. Once such a ligand is attached to a vesicle, the unoccupied specificity ("monospecificity") of the ligand pertains until it interacts with the target (tumor) mammalian cell.

The ligand can be attached to the cell membrane of the vesicles by virtue of the interaction between the ligand and a component on the cell membrane, such as a polysaccharide, a glycoprotein, or a polypeptide. The expressed ligand is anchored on the surface of a vesicle such that the surface component-binding portion of the ligand is exposed so that the portion can bind the target mammalian cell surface component when the vesicle and the mammalian cell come into contact.

Alternatively, the ligand can be expressed and displayed by a living counterpart of a bacterially derived vesicle, e.g., by the parent cell of a minicell or by a bacterial cell before it becomes a killed cell. In this instance the ligand does not require a specificity to the vesicle and only displays a specificity to a component that is characteristic of mammalian cells. That is, such component need not be unique to tumor cells, per se, or even to the particular kind of tumor cells under treatment, so long as the tumor cells present the component on their surface.

Upon intravenous administration, vesicles accumulate rapidly in the tumor microenvironment. This accumulation, occurring as a function of the above-described leaky tumor vasculature, effects delivery of vesicle-packaged therapeutic payload to cells of the tumor, which then internalize packaged vesicles.

The inventors have found that this delivery approach is applicable to a range of mammalian tumor cells, including cells that normally are refractory to specific adhesion and endocytosis of minicells. For instance, ligands that comprise an antibody directed at an anti-HER2 receptor or anti-EGF receptor can bind minicells to the respective receptors on a range of targeted non-phagocytic cells, such as lung, ovarian, brain, breast, prostate, and skin cancer cells.

The binding thus achieved precedes uptake of the vesicles by each type of non-phagocytic cells. That is, in the context of the present invention a suitable target cell presents a cell surface component the binding of which, by a ligand on a vesicle, elicits endocytosis of that vesicle.

More specifically, the present inventors discovered that the interaction between (a) the ligand on a minicell or a killed bacterial cell and (b) a mammalian cell surface receptor can activate an uptake pathway, called here a "receptor-mediated endocytosis" (rME) pathway, into the late-endosomal/lysosomal compartment of the target host cell, such as a tumor cell. By this rME pathway, the inventors found, bacterially derived vesicles are processed through the early endosome, the late endosome and the lysosome, resulting in release of their payload into the cytoplasm of the mammalian host cell. Moreover, a payload that is a nucleic acid not only escapes complete degradation in the late-endosomal/lysosomal compartment but also is expressed by the host cell.

A ligand for this delivery approach can be "bispecific," as described above, because it binds to surface components on a payload-carrying vesicle and on a target cell, respectively, and its interaction with the latter component leads to uptake of the vesicle into the rME pathway. In any event, a given target cell-surface component can be a candidate for binding by the ligand, pursuant to the invention, if interaction with the component in effect accesses an endocytic pathway that entails a cytosolic internalization from the target cell surface. Such candidates are readily assessed for suitability in the invention via an assay in which a cell type that presents on its surface a candidate component is co-incubated in vitro with minicells carrying a ligand that binds the candidate and that also is joined to a fluorescent dye or other marker amenable to detection, e.g., visually via confocal microscopy. (An in vitro assay of this sort is described by MacDiarmid et al. (2007), in the legend to FIG. 3 at page 436.) Thus, an observed internalization of the marker constitutes a positive indication by such an assay that the tested target cell-surface component is suitable for the present invention.

Illustrative of candidate target cell-surface components are members of (A) the receptor tyrosine kinases or "RKTs," a family of transmembrane proteins that undergo constitutive internalization (endocytosis) at a rate similar to that of other integral membrane proteins. See Goh and Sorkin, *Cold Spring Harb. Perspect. Biol.* 5: a017459 (2013). The family of RKTs is described by Lemmon and Schlessinger, *Cell* 141(7): 1117-134 (2010). The table below lists, in twenty subfamilies, all fifty-eight RTKs in the human proteome, any one or more of which may be tested for suitability in the invention, as described above (see also FIG. 7).

| RTK Subfamilies | Exemplary RTKs |
|---|---|
| ErbB | EGFR, ErbB2, ErbB3, ErbB4 |
| Ins | InsR, IGF1R, InsRR |
| PDGF | PDGFRα, PDGFRβ, CSF1R/Fms, Kit/SCFR, Fit3/Flk2 |
| VEGF | VEGFR1/Fit1, VEGFR2/KDR, VEGFR3/Fit4 |
| FGF | FGFR1, FGFR2, FGFR3, FGFR4 |
| PTK7 | PTK7/CCK4 |
| Trk | TrkA, TrkB, TrkC |
| Ror | Ror1, Ror2 |
| MuSK | MuSK |
| Met | Met, Ron |
| Axl | Axl, Mer, Tyro3 |
| Tie | Tie1, Tie2 |
| Eph | EphA1-8, EphA10, EphB1-4, EphB6 |
| Ret | Ret |
| Ryk | Ryk |
| DDR | DDR1, DDR2 |
| Ros | Ros |
| LMR | LMR1, LMR2, LMR3 |
| ALK | ALK, LTK |
| STYK1 | SuRTK106/STYK1 |

Likewise illustrative are members of: (B) the class of membrane-associated, high-affinity folate binding proteins (folate receptor), which bind folate and reduced folic acid derivatives and which mediate delivery of tetrahydrofolate to the interior of cells, (C) the subgroup of membrane-bound cytokine receptors that play a role in the internalization of a cognate cytokine, such as IL13; (D) the surface antigens, such as CD20, CD33, mesothelin and HM1.24, that are expressed on certain cancer cells and that mediate the internalization of cognate monoclonal antibodies, e.g., rituximab in the instance of CD20; and (E) the family of adhesion receptors (integrins), transmembrane glyproteins that are trafficked through the endosomal pathway and are major mediators of cancer cell adhesion to extracellular matrix.

In accordance with the invention, the ligand can be any polypeptide or polysaccharide that exhibits the desired specificity or specificities, as the case may be. Preferred ligands are antibodies. In its present use the term "antibody" encompasses an immunoglobulin molecule obtained by in vitro or in vivo generation of an immunogenic response. Accordingly, the "antibody" category includes monoclonal antibodies and humanized antibodies, such as single-chain antibody fragments (scFv), bispecific antibodies, etc. A large number of different bispecific protein and antibody-based ligands are known, as evidenced by the review article of Caravella and Lugovskoy, *Curr. Opin. Chem. Biol.* 14: 520-28 (2010), which is incorporated here by reference in its entirety. Antibodies useful in accordance with the present disclosure can be obtained as well by known recombinant DNA techniques.

By way of non-limiting example, therefore, an antibody that carries specificity for a surface component, such as a tumor antigen, can be used to target minicells to cells in a tumor to be treated, pursuant to the invention. Illustrative cell surface receptors in this regard include any of the RTKs epidermal growth factor receptor (EGFR), vascular endothelial growth factor receptor (VEGFR), platelet-derived growth factor receptor (PDGFR) and insulin-like growth factor receptor (IGFR), each of which is highly expressed in several solid tumors, including brain tumors, and folate receptor, which is overexpressed in some pituitary adenomas. Such a bispecific ligand can be targeted as well to mutant or variant receptors, e.g., the IL-13Rα2 receptor, which is expressed in 50% to 80% of human glioblastoma multiforme tumors, see Wykosky et al., *Clin Cancer Res.* 14: 199-208 (2008), Jarboe et al., *Cancer Res.* 67: 7983-86

(2007), Debinski et al., *J. Neurooncol.* 48: 103-11 (2000), and Okada et al., *J. Bacteriol.* 176: 917-22 (1994), but which differs from its physiological counterpart IL4R/IL13R, expressed in normal tissues. See Hershey, *J. Allergy Clin. Immunol.* 111: 677-90 (2003). Thus, IL13Rα2 is virtually absent from normal brain cells. See Debinski and Gibo, *Mol. Med.* 6: 440-49 (2000). Additionally, tumors that metastasize to the brain may overexpress certain receptors, which also can be suitable targets. For instance, Da Silva et al., *Breast Cancer Res.* 12: R46 (1-13) (2010), showed that brain metastases of breast cancer expressed all members of the HER family of RTKs. HER2 was amplified and overexpressed in 20% of brain metastases, EGFR was overexpressed in 21% of brain metastases, HER3 was overexpressed in 60% of brain metastases and HER4 was overexpressed in 22% of brain metastases. Interestingly, HER3 expression was increased in breast cancer cells residing in the brain.

(H) Agents to Increase the Levels of Ifn-Gamma

The present compositions and methods can further include an agent that increases the level (e.g., the activity or expression level) of IFN-gamma in a patient.

In one embodiment, the agent includes an IFN-gamma protein or analog. Commercial products of IFN-gamma, such as Actimmune®, are or will be available. Actimmune® is a bioengineered form of interferon gamma, a protein that acts as a biologic response modifier through stimulation of the human immune system. As noted above, the FDA has approved Actimmune® for use in children and adults with chronic granulomatous disease and severe, malignant osteopetrosis.

IFN-gamma production is controlled by cytokines secreted by APCs, most notably interleukin (IL)-12 and IL-18. These cytokines serve as a bridge to link infection with IFN-gamma production in the innate immune response. Macrophage recognition of many pathogens induces secretion of IL-12 and chemokines. These chemokines attract NK cells to the site of inflammation, and IL-12 promotes IFN-gamma synthesis in these cells. In macrophages, NK and T cells, the combination of IL-12 and IL-18 stimulation further increases IFN-gamma production. Accordingly, any of these proteins or their combinations are suitable agents for the purpose of this disclosure.

Negative regulators of IFN-gamma production include IL-4, IL-10, transforming growth factor-β, and glucocorticoids. Proteins or nucleic acids that inhibit these factors will be able to stimulate the production of IFN-gamma.

Also suitable for use in this context are polynucleotides that encode IFN-gamma or genes that activate the production and/or the secretion of IFN-gamma.

The agent that increases the level of IFN-gamma also can be a viral vaccine. A number of viral vaccines are available that can induce IFN-gamma production without causing infection or other types of adverse effects. Illustrative of this class of viral-vaccine agent is a flu (influenza) vaccine.

The data show that the serum concentration of IFN-gamma required for effectively activating host immune response to tumor cells is low, when the patient also receives administration of drug-loaded, bispecific antibody-targeted minicells or killed bacterial cells. Thus, in one aspect the inventive methodology results in increase of serum IFN-gamma concentration that is not higher than about 30,000 pg/mL. In another aspect, the serum IFN-gamma concentration is increased to not higher than about 5000 pg/mL, 1000 pg/mL, 900 pg/mL, 800 pg/mL, 700 pg/mL, 600 pg/mL, 500 pg/mL, 400 pg/mL, 300 pg/mL, 200 pg/mL, or 100 pg/mL. In a further aspect, the resulting serum IFN-gamma concentration is at least about 10 pg/mL, or at least about 20 pg/mL, 30 pg/mL, 40 pg/mL, 50 pg/mL, 60 pg/mL, 70 pg/mL, 80 pg/mL, 90 pg/mL, 100 pg/mL, 150 pg/mL, 200 pg/mL, 300 pg/mL, 400 pg/mL or 500 pg/mL.

Pursuant to some aspects, the agent is an IFN-gamma protein, engineered protein or analog. In some aspects, the administration achieves from about 0.02 ng to 1 microgram of IFN-gamma per ml of host blood. In one aspect, the achieved IFN-gamma concentration in the host blood is from about 0.1 ng to about 500 ng per ml, or from about 0.2 ng to about 200 ng per ml, or from about 0.5 ng to about 100 ng per ml, or from about 1 ng to about 50 ng per ml, or from about 2 ng to about 20 ng per ml. The therapeutic dose of IFN-gamma in the composition of the present disclosure can be determined accordingly.

(I) Formulations and Administration Routes and Schedules

Formulations of a composition of the disclosure can be presented in unit dosage form, e.g., in ampules or vials, or in multi-dose containers, with or without an added preservative. The formulation can be a solution, a suspension, or an emulsion in oily or aqueous vehicles, and can contain formulatory agents, such as suspending, stabilizing and/or dispersing agents. A suitable solution is isotonic with the blood of the recipient and is illustrated by saline, Ringer's solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for instance, subcutaneously or intramuscularly) or by intramuscular injection.

In some aspects, a minicell- or killed bacterial cell-containing composition that includes a therapeutically effective amount of an anti-neoplastic agent is provided. A "therapeutically effective" amount of an anti-neoplastic agent is a dosage of the agent in question, e.g., a siRNA or a chemotherapeutic drug that invokes a pharmacological response when administered to a subject, in accordance with the present disclosure.

In some aspects, a composition is provided that includes a therapeutically effective amount of an agent that increases the level of IFN-gamma. In some aspects, a composition, kit, package or product is provide that includes both a minicell or killed bacterial cell as described and an agent that increases the level of IFN-gamma.

In the context of the present disclosure, therefore, a therapeutically effective amount can be gauged by reference to the prevention or amelioration of the tumor or a symptom of tumor, either in an animal model or in a human subject, when minicells or killed bacterial cells carrying a therapeutic payload are administered, as further described below. An amount that proves "therapeutically effective amount" in a given instance, for a particular subject, may not be effective for 100% of subjects similarly treated for the tumor, even though such dosage is deemed a "therapeutically effective amount" by skilled practitioners. The appropriate dosage in this regard also will vary as a function, for example, of the type, stage, and severity of the tumor. Likewise, when "therapeutically effective" is used to refer to the number of minicells in a pharmaceutical composition, the number can be ascertained based on what anti-neoplastic agent is packaged into the minicells and the efficacy of that agent in treating a tumor. The therapeutic effect, in this regard, can be measured with a clinical or pathological parameter such as tumor mass. A reduction or reduced increase of tumor mass, accordingly, can be used to measure therapeutic effects.

With respect to the agent that increases the level of IFN-gamma, a "therapeutically effective amount" can refer to the amount of the agent, upon administration, achieves the desired host blood concentration, as provided supra.

Formulations within the disclosure can be administered via various routes and to various sites in a mammalian body, to achieve the therapeutic effect(s) desired, either locally or systemically. In a particular aspect, the route of administration is intravenous injection.

In general, formulations of the disclosure can be used at appropriate dosages defined by routine testing, to obtain optimal physiological effect, while minimizing any potential toxicity. The dosage regimen can be selected in accordance with a variety of factors including age, weight, sex, medical condition of the patient; the severity or stage of tumor, the route of administration, and the renal and hepatic function of the patient.

Optimal precision in achieving concentrations of minicell, killed bacterial cell, and therapeutic agent within the range that yields maximum efficacy with minimal side effects can and typically will require a regimen based on the kinetics of agent availability to target sites and target cells. Distribution, equilibrium, and elimination of minicells or agent can be considered when determining the optimal concentration for a treatment regimen. The dosage of minicells and therapeutic agent, respectively, can be adjusted to achieve desired effects.

Moreover, the dosage administration of the formulations can be optimized using a pharmacokinetic/pharmacodynamic modeling system. Thus, one or more dosage regimens can be chosen and a pharmacokinetic/pharmacodynamic model can be used to determine the pharmacokinetic/pharmacodynamic profile of one or more dosage regimens. Based on a particular such profile, one of the dosage regimens for administration then can be selected that achieves the desired pharmacokinetic/pharmacodynamic response. For example, see WO 00/67776.

The minicells or killed bacterial cells packaged with an anti-neoplastic agent and the agent that increases the level of IFN-gamma can be administered concurrently, either in a combination formulation or as separate compositions, or sequentially one after the other. When administered sequentially, the minicells or killed bacterial cells can be administered before the agent that increases the level of IFN-gamma, or afterwards. In one aspect, when the minicells or killed bacterial cells reach maximum plasma level or effective plasma level following administration, the host has achieved or is maintaining a minimum level of IFN-gamma. Such a minimum level is one that is required to produce synergism between the compositions. This can be achieved by administering the agent that increases the IFN-gamma level before administering the minicells or killed bacterial cells, or by administering the agent shortly after the minicells or killed bacterial cells are administered, in particular at a relatively high dose. It is noted that administration of both compositions can take place in series. In that respect, then, the administrations result in constant exposure of the host to both the minicells or killed bacterial cells and the agent that increases IFN-gamma.

A formulation or combination of formulations of the disclosure can be administered at least once a week to a tumor patient, over the course of several weeks. Thus, the formulation can be administered at least once a week, over a period of several weeks to several months.

More specifically, inventive formulations can be administered at least once a day for about 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. Alternatively, the formulations can be administered about once every day or about once every 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days or more.

In another embodiment of the disclosure, formulations can be administered about once every week or about once every 2, 3, 4, 5, 6, 7, 8, 9, 10, 11, 12, 13, 14, 15, 16, 17, 18, 19 or 20 weeks or more. Alternatively, the formulations can be administered at least once a week for about 2, 3, 4, 5, 6, 7, 8, 9, 10, 11, 12, 13, 14, 15, 16, 17, 18, 19 or 20 weeks or more.

Alternatively, the formulations can be administered about once every month or about once every 2, 3, 4, 5, 6, 7, 8, 9, 10, 11 or 12 months or more.

The formulations can be administered in a single daily dose. Alternatively, the total daily dosage can be administered in divided doses of two, three, or four times daily.

The following examples are illustrative only, rather than limiting, and provide a more complete understanding of the disclosure.

EXAMPLE 1

Tumor Size Reduction Correlated with Interferon-gamma Levels

This example demonstrates that the reduction of brain tumor volumes in dogs undergoing treatments with drug-loaded minicells correlated with the expression level of interferon-gamma (IFNγ). This example, therefore, suggests that IFN-gamma increases the efficacy of drug-loaded minicells. Given the low amount of IFN-gamma needed, this example further suggests synergism between IFN-gamma and drug-loaded, bispecific antibody-targeted minicells.

Materials and Methods

Preparation and Dosing of Doxorubicin-packaged, Canine EGFR-targeted Minicells

Minicells were derived from a minCDE-chromosomal deletion mutant of *Salmonella enterica* serovar *Typhimurium, S. typhimurium*, purified, packaged with doxorubicin (dox) and targeted via attachment of a bispecific monoclonal antibody (MAb) comprising anti-minicell surface O-polysaccharide and anti-canine EGFR specificities, (designated, $^{EGFR}$minicells$_{Dox}$).

Dogs in this study were pet dogs presenting as patients to the Veterinary Specialist Centre (VSC) or the Small Animal Specialist Hospital (SASH), in Sydney, Australia. Study participation was offered to patients where standard therapy had been declined by the dog's owner or, in cases of advanced disease, where no meaningful standard therapy existed. Dogs were treated in compliance with guidelines promulgated by the National Health and Medical Research Council (Australia) for the care and use of laboratory animals, and with EnGeneIC Animal Ethics Committee approval. Signed informed consent was obtained from all owners.

All brain tumors were diagnosed by histology or cytology where feasible. Antemortem diagnoses were based on a combination of characteristic appearance on magnetic resonance imaging (MRI) and clinical signs. Histological diagnosis was deemed too invasive in these brain tumor cases and diagnosis was confirmed by necropsy.

Treatment with 1×10$^{10}$ $^{EGFR}$minicells$_{Dox}$ per dose was performed on a weekly basis. Treatment was administered via an aseptically placed peripheral vein catheter (left cephalic) in 2 ml over a 2 minute infusion.

MRI Tumor Imaging

Tumor images were performed at Specialist Magnetic Resonance Imaging using a Philips 1.5T Achieva scanner. The protocol used an 8-channel head coil or 8-channel knee coil depending on the size of the dog (small dogs used the knee coil).

Sequences were obtained from sagittal T1, axial T2, Coronal Gradient Echo, axial diffusion weighted images (DWI) pre contrast, coronal volumetric fluid-attenuated inversion recovery (FLAIR) and post gadolinium T1 weighted images obtained in three planes.

IFN-gamma Enzyme-linked Immunosorbent Assay (ELISA)

Blood was taken before minicell dose and serum received directly from the veterinary clinic. IFN-gamma measurement performed in duplicate using Canine IFN-gamma DuoSet® ELISA Kit from R & D Systems (#DY781B) as per the manufacturer's instructions.

Results

Figure 1A:
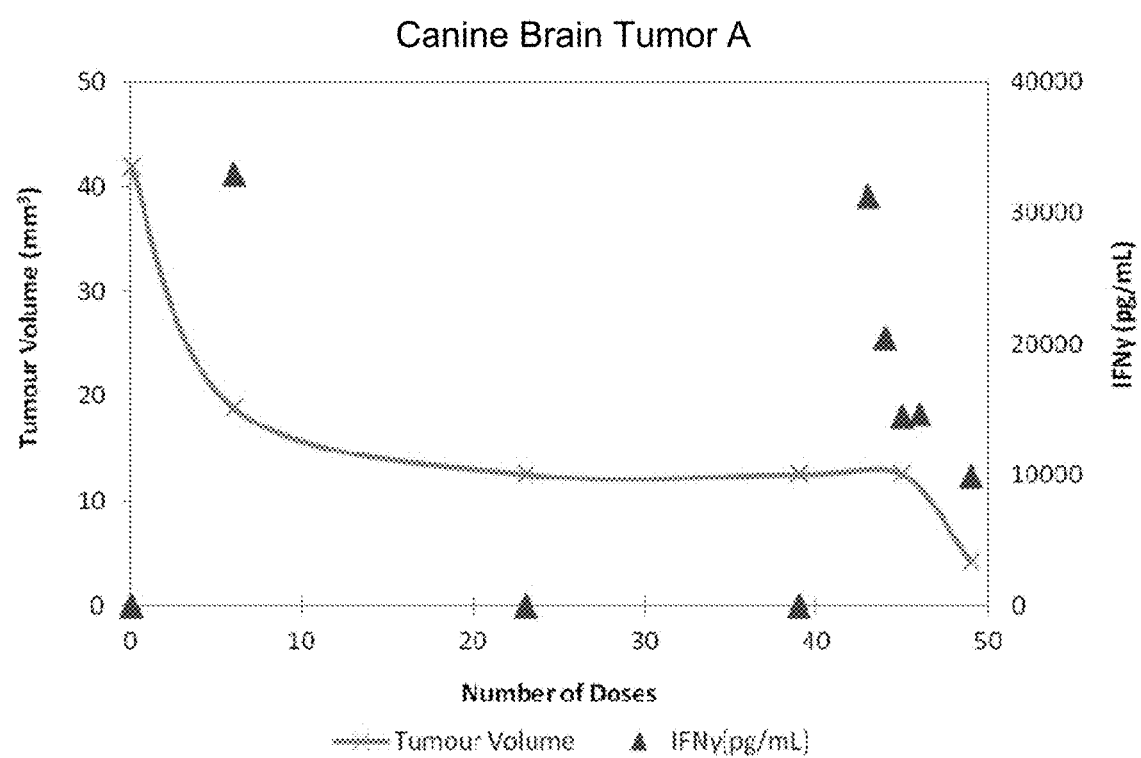
FIG. 1A-1C present charts of tumor volumes (y axis on the left) and serum IFN-gamma concentrations (y axis on the right), measured at different time points (x axis, shown as number of doses), for three dogs A, B, and C, respectively.
Figure 1B:
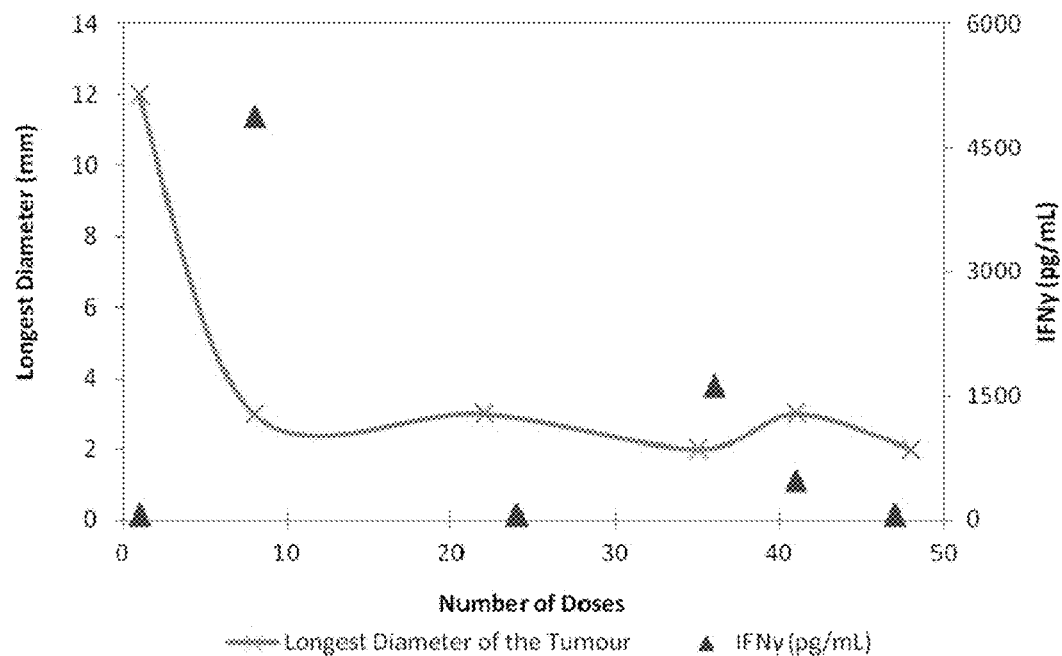
Figure 1C:
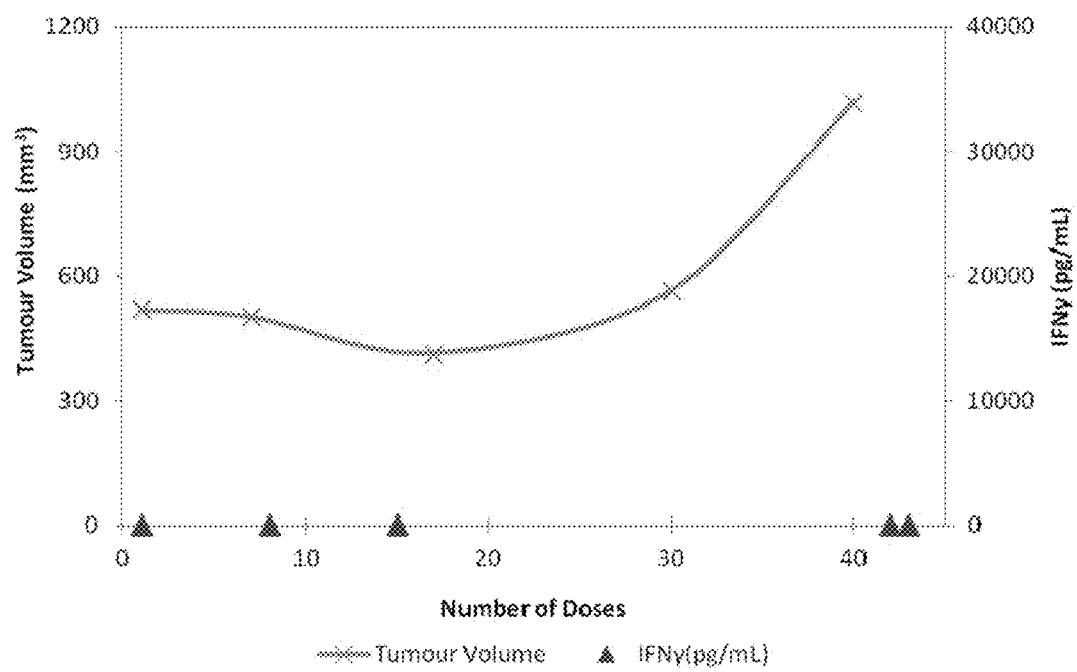

The results, in terms of tumor volume changes, in three dogs receiving the minicell treatments are presented in FIG. 1A-1C. The line graphs represent tumor measurements (lefty axis=volume in (mm$^3$) or longest diameter (mm)) as a function of the number of minicells doses (x axis). Crosses represent the doses at which the tumors were visualized and measured by magnetic resonance imaging (MRI).

During the treatment, two of the dogs showed drastic reduction in tumor volumes in certain treatment periods (dogs A and B in FIGS. 1A and 1B). It was discovered unexpectedly that the dogs were suffering from viral infections during those periods. Among a number of parameters examined that might be associated with viral infection, it was found that the serum concentration of IFN-gamma highly correlated with the tumor volume reduction rates.

In each of FIG. 1A-1C, the triangular markers represent serum interferon gamma (IFNγ) levels; measured at the indicated doses by ELISA. The right-handy axis indicates IFN-gamma levels in pg/mL. Where the assay was performed but IFN-gamma was below the detection limit of the assay (<56 pg/mL), the data points are represented by triangular markers at 0 pg/mL. Where tumor length (l), width (w) and height (h) measurements were made, the tumor volume (V) was calculated using the ellipsoid formula (V=(π/6)*l*w*h).

These figures thus demonstrate a strong correlation between serum IFN-gamma levels and brain tumor volume reduction rates. What also is surprising is that any detectable IFN-gamma levels led to increased anti-tumor response. The lowest IFN-gamma level directed was about 500 pg/mL, at dose 41 in dog B (FIG. 1B). Such a drastic effect of IFN-gamma on the tumor treatment of drug-loaded minicells is a strong indication of synergism between them.

EXAMPLE 2

Significant Tumor Regression in Mouse Xenografts (Human Alveolar Adenocarcinoma) Following Treatment with $^{EGFR}$Minicells$_{Dox}$ and IFN-gamma This example demonstrates that combined treatment with bispecific ligand-targeted and doxorubicin-packaged intact minicells with IFN-gamma can effect regression of human alveolar adenocarcinoma tumor xenografts established in 6 week-old female athymic nude mice.

As described above, minicells were produced from an *S. typhimurium* minCDE-mutant strain and were purified using a gradient centrifugation/filamentation/filtration/endotoxin removal procedure previously described in MacDiarmid et al. (2007). The purified minicells were packaged with chemotherapeutic drug doxorubicin, also per MacDiarmid et al. (2007).

The bispecific antibody (BsAb) was a single polypeptide containing binding specificity respectively for *S. typhimurium* O-polysaccharide, present on minicells, and for human EGFR, overexpressed on alveolar adenocarcinoma cells. The O-polysaccharide specificity was derived from a mouse monoclonal antibody, for which the variable regions were isolated from a hybridoma cell line and presented as a single-chain variable fragment (scFv). The hybridoma cell line was prepared by immunizing mice with purified LPS and fusing the lymphocytes with tumor cells. Subsequently, the clones were screened for an antibody capable of binding the O-polysaccharide. The EGFR specificity, also presented as an scFv, was derived from the commercial antibody Erbitux® (Bristol Myers Squibb, USA). The two scFv components were separated by a flexible linker and a 6×His tag incorporated at the N-terminus, to facilitate purification by immobilized metal affinity chromatography, and a c-myc tag at the C-terminus, to aid in additional detection. Linkers connecting the scFv components are well known, as evidenced by Gall et al., *Protein Engineering, Design and Selection* 17: 357-66 (2004), for example.

The expression vector encoding the BsAb contains an hCMV promoter for high-level expression and a signal peptide for the secretion of the BsAb into the cell culture medium. The expression vector encoding the BsAb is stably transfected into suspension adapted Chinese hamster ovary (CHO) cells in chemically defined, protein and animal origin free medium and the protein is expressed over 10 days in culture.

Two chromatographic columns were used to purify the antibody: an immobilized metal ion affinity chromatography column (IMAC- HisTrap™ Excel, GE Life Sciences) and a hydroxyapatite chromatography column (BioRad CHT™ I). This approach achieved an antibody purity of >98%. For viral safety of product, the antibody was put through a solvent/detergent inactivation, using TNBP/Tween®, and a viral filtration. The final yield of antibody was 10 mg from 1 L of cell culture supernatant.

The mice used in this example were purchased from Animal Resources Centre (Perth, Australia), and all animal experiments were performed in compliance with GUIDE OF CARE AND USE OF LABORATORY ANIMALS, 8$^{th}$ ed. (National Academies Press, 2011) and with Animal Ethics Committee approval. The experiments were performed in the NSW Agriculture-accredited small animal facility at EnGeneIC Ltd. (Sydney, Australia).

Human alveolar adenocarcinoma cells (A549, ATCC) were grown in tissue culture to full confluency in T-75 flasks in GIBCO®-RPMI 1640 medium, a product of Life Technologies (Carlsbad, Calif., USA), supplemented with 5% bovine calf serum and glutamine, in a humidified atmosphere of 95% air and 5% $CO_2$ at 37° C. Cells (1×10$^6$) in 50 µL serum-free medium with 50 µL growth factor reduced Matrigel®, product of BD Biosciences (Franklin Lakes, N.J.). The cells then were injected subcutaneously, using a 23-gauge needle, between the shoulder blades of each mouse.

The resulting tumors were measured twice a week, using an electronic digital caliper (Mitutoyo, Japan, with a measure accuracy of +/−0.001 inch), and mean tumor volume was calculated using the formula length (mm)×width (mm$^2$)×0.5=volume (mm$^3$).

The treatments commenced when the tumors reached a mean of ~285 mm$^3$, and mice were randomized to four different groups of seven mice per group. All treatments were administered intravenously (i.v.) in a total volume of 100 µl. All minicell doses contained 1×10$^9$ minicells of the respective type.

In terms of experimental design, Group 1 (control) received no sterile physiological saline. Group 2 (control) received IFN-gamma (0.5×10$^4$ IU) per dose. Group 3 (control) received $^{EGFR}$minicells$_{Dox}$. Group 4 (experimental) received $^{EGFR}$minicells$_{Dox}$ and IFN-gamma (0.5×10$^4$ IU) per dose.

The results (FIG. 2) revealed that mice treated with $^{EGFR}$minicells$_{Dox}$ (Group 3) achieved tumor stabilization. By contrast, mice treated with $^{EGFR}$minicells$_{Dox}$ and IFN-gamma (Group 4) showed highly significant tumor regression by day 43, after a total of six doses. Mice treated with IFN-gamma alone (Group 2) showed no anti-tumor efficacy, and the tumors grew as in the saline treated group (Group 1).

EXAMPLE 3

Significant Tumor Regression in Mouse Xenografts (Human Breast Cancer—Moderate Sized Tumors~145 mm$^3$) after Treatment with $^{EGFR}$Minicells$_{Dox}$ and IFN-gamma This example demonstrates that combined treatment with bispecific ligand-targeted and doxorubicin-packaged intact minicells with IFN-gamma can effect regression of human breast tumor xenografts established in 6 week-old female athymic nude mice.

As described above, minicells were purified, packaged with doxorubicin, and targeted using single chain bispecific antibody with anti-O-polysaccharide and anti-EGFR specificities. Additionally, human breast cancer cells (MDA-MB-468; ATCC) were established as xenografts in nu/nu mice, and tumor volumes were measured, also as described.

The treatments commenced when the tumors reached a mean of ~145 mm$^3$, and mice were randomized to four different groups of seven mice per group. All treatments were administered i.v. in a total volume of 100 µl. All minicell doses contained 1×10$^9$ minicells of the respective type.

The experiment was designed as follows: Group 1 (control) received sterile physiological saline only. Group 2 (control) received IFN-gamma (0.5×10$^4$ IU) per dose. Group 3 (control) received $^{EGFR}$minicells$_{Dox}$. Group 4 (experimental) received $^{EGFR}$minicells$_{Dox}$ and IFN-gamma (0.5×10$^4$ IU) per dose.

The results as shown in FIG. 3 revealed that mice treated with $^{EGFR}$minicells$_{Dox}$ (Group 3) achieved tumor stabilization, but by about day 25 the tumors began to grow again, probably due to development of resistance to doxorubicin. By contrast, mice treated with $^{EGFR}$minicells$_{Dox}$ and IFN-gamma (Group 4) showed highly significant tumor regression, and by day 30 these tumors, after a total of six doses, were more like scar tissue. Mice treated with IFN-gamma alone (Group 2) showed no anti-tumor efficacy, and the tumors grew as in the saline treated group (Group 1).

EXAMPLE 4

Significant Tumor Regression in Mouse Xenografts (Human Breast Cancer—Large Tumors—250 mm$^3$) after Treatment with $^{EGFR}$Minicells$_{Dox}$ and IFN-gamma This example demonstrates that combined treatment of with bispecific ligand-targeted and doxorubicin-packaged intact minicells with IFN-gamma can effect regression even in large sized tumors (~250 mm$^3$) of human breast tumor xenografts established in 6 week-old female athymic nude mice.

As described above, minicells were purified, packaged with doxorubicin and targeted using single chain bispecific antibody with anti-O-polysaccharide and anti-EGFR specificities. Human breast cancer cells (MDA-MB-468) were established as xenografts in nu/nu mice, and tumor volumes were measured, also as described above.

The treatments were begun when the tumors reached a mean of ~250 mm$^3$. As above, mice were randomized to four different groups of seven mice per group. The i.v. administration and minicell doses were as above, too.

The experiment was designed as follows. Group 1 (control) received sterile physiological saline only. Group 2 (control) received IFN-gamma (0.5×10$^4$ IU) per dose. Group 3 (control) received $^{EGFR}$minicells$_{Dox}$. Group 4 (experimental) received $^{EGFR}$minicells$_{Dox}$ and IFN-gamma (0.5×10$^4$ IU) per dose.

The results as shown in FIG. 4 revealed that mice treated with $^{EGFR}$minicells$_{Dox}$ (Group 3) achieved tumor regression but that by ~day 23 the tumors had begun to grow again; as before, development of doxorubicin resistance was the likely cause. On the other hand, mice treated with $^{EGFR}$minicells$_{Dox}$ and IFN-gamma (Group 4) showed highly significant tumor regression, and after a total of 3 doses (i.e., by day 28) these tumors were more like scar tissue. Mice treated with IFN-gamma alone (Group 2) showed no anti-tumor efficacy and the tumors grew as in the saline treated group (Group 1).

EXAMPLE 5

Tumor Regression in Mouse Xenografts (Human Breast Cancer—Very Large Tumors ~250 mm$^3$ to 600 mm$^3$) after Treatment with $^{EGFR}$Minicells$_{Dox}$ and IFN-gamma This example demonstrates that combined treatment with bispecific ligand-targeted and doxorubicin-packaged intact minicells with IFN-gamma can effect regression even in very large sized tumors (~250 mm$^3$ to 600 mm$^3$) of human breast tumor xenografts established in 6 week old female athymic nude mice.

As described above, minicells were purified, packaged with doxorubicin and targeted using single chain bispecific antibody with anti-O-polysaccharide and anti-EGFR specificities. Also as described, human breast cancer (MDA-MB-468) cells were established as xenografts in nu/nu mice, and tumor volumes were measured.

The treatments were commenced when the tumors reached ~250 mm$^3$ to 600 mm$^3$. Individual mice were treated with $^{EGFR}$minicells$_{Dox}$ and IFN-gamma (0.5×10$^4$ IU) per dose. All treatments were administered i.v. in a total volume of 100 µl, and all minicell doses contained $1\times10^9$ minicells of the respective type.

The results are depicted in FIG. 5. Notwithstanding the large size of the tumors, all four mice achieved tumor regression. This shows that even very large tumors (~600 mm³), where mice would normally be euthanized, can be treated effectively with the combination of $^{EGFR}$minicells$_{Dox}$ and IFN-gamma ($0.5\times10^4$ IU).

EXAMPLE 6

Significant Tumor Regression in Mouse Xenografts (Human Alveolar Adenocarcinoma) after Treatment with $^{EGFR}$Minicells$_{Dox}$ and Two Dose Levels of IFN-gamma This example demonstrates that combined treatment with bispecific ligand-targeted and doxorubicin-packaged intact minicells with IFN-gamma at two different dose levels can effect regression of human alveolar adenocarcinoma xenografts established in 6 week-old female athymic nude mice.

As described above, minicells were purified, packaged with doxorubicin and targeted using single chain bispecific antibody with anti-O-polysaccharide and anti-EGFR specificities. Human alveolar adenocarcinoma (A549) cells were established as xenografts in nu/nu mice, and tumor volumes were measured, also as described above.

The treatments commenced when the tumors reached a mean of ~100 mm³, and mice were randomized to four different groups of seven mice per group. All treatments were administered i.v. in a total volume of 100 µl. All minicell doses contained $1\times10^9$ minicells of the respective type.

Group 1 (control) received no sterile physiological saline. Group 2 (control) received $^{EGFR}$minicells$_{Dox}$ (twice per week). Group 3 (experimental) received $^{EGFR}$minicells$_{Dox}$ and IFN-gamma ($0.75\times10^4$ IU) per dose, twice per week. Group 4 (experimental) received $^{EGFR}$minicells$_{Dox}$ and IFN-gamma ($0.5\times10^4$ IU) per dose, three per week.

As FIG. 6 shows, mice treated with $^{EGFR}$minicells$_{Dox}$ and IFN-gamma at both doses ($0.5\times10^4$ IU and $0.75\times10^4$ IU; Groups 3 and 4) achieved tumor stabilization. By contrast, mice treated with $^{EGFR}$minicells$_{Dox}$ (Group 2) showed no anti-tumor efficacy, and the tumors grew as in the saline treated group (Group 1). These data demonstrate that combining IFN-gamma with $^{EGFR}$minicells$_{Dox}$ was essential at both IFN-gamma dose levels to achieve tumor stabilization in the treatment of tumors that normally are resistant to either IFN-gamma treatment alone or $^{EGFR}$minicells$_{Dox}$ treatment alone.

The invention claimed is:

1. A method for treating a tumor in a subject, comprising administering to the subject:
   (a) a first composition comprising intact bacterial minicells, each of which encompasses an anti-neoplastic agent and carries a ligand on the surface of the intact bacterial minicells, wherein (i) the ligand has specificity to a non-phagocytic mammalian cell surface receptor, (ii) the antineoplastic agent is selected from the group consisting of a radionuclide, a chemotherapy drug, a functional nucleic acid selected from the group consisting of siRNA, miRNA, shRNA, lincRNA, antisense RNA, and ribozyme, and a polynucleotide from which a functional nucleic acid selected from the group consisting of siRNA, miRNA, shRNA, lincRNA, antisense RNA, and ribozyme is transcribed, and
   (b) a second composition comprising interferon-gamma (IFN-gamma) or an agent that increases the expression of IFN-gamma in the subject, wherein the agent that increases the expression of IFN-gamma is a viral vaccine that induces IFN-gamma expression or a polynucleotide encoding IFN-gamma, wherein the first and second compositions are administered concurrently or sequentially.

2. The method of claim 1, wherein the second composition comprises purified IFN-gamma protein.

3. The method of claim 1, wherein the first composition comprises from about $10^9$ to about $10^{10}$ minicells or killed bacterial cells.

4. The method of claim 1, wherein the anti-neoplastic agent is a radionuclide.

5. The method of claim 1, wherein the anti-neoplastic agent is a chemotherapy drug.

6. The method of claim 5, wherein the chemotherapy drug is a small molecule drug having a molecular weight of less than about 900 Dalton.

7. The method of claim 6, wherein the small molecule drug is cytotoxic.

8. The method of claim 7, wherein the small molecule drug is a morpholinyl anthracycline derivative.

9. The method of claim 8, wherein the small molecule drug is PNU-159682.

10. The method of claim 1, wherein said anti-neoplastic agent is a functional nucleic acid selected from the group consisting of siRNA, miRNA, shRNA, lincRNA, antisense RNA, and ribozyme, and a polynucleotide from which a functional nucleic acid selected from the group consisting of siRNA, miRNA, shRNA, lincRNA, antisense RNA, and ribozyme is transcribed.

11. The method of claim 10, wherein said functional nucleic acid inhibits a gene that promotes tumor cell proliferation, angiogenesis or resistance to chemotherapy and/or that inhibits apoptosis or cell cycle arrest.

12. The method of claim 10, wherein said functional nucleic acid is siRNA or miRNA.

13. The method of claim 10, wherein the functional nucleic acid inhibits the gene ribonucleotide reductase M1 (RRM1).

14. A method for treating a tumor in a subject, comprising administering to the subject a composition comprising intact bacterial minicells, each of which encompasses an anti-neoplastic agent and carries a ligand on the surface of the intact minicells, wherein the ligand has specificity to a non-phagocytic mammalian cell surface receptor, and
   wherein the anti-neoplastic agent is a functional nucleic acid selected from the group consisting of siRNA, miRNA, shRNA, lincRNA, antisense RNA, and ribozyme, or the anti-neoplastic agent is a polynucleotide from which a functional nucleic acid selected from the group consisting of siRNA, miRNA, shRNA, lincRNA, antisense RNA, and ribozyme is transcribed; and
   wherein the functional nucleic acid inhibits the gene ribonucleotide reductace M1 (RRM1).

15. The method of claim 14, wherein the composition comprises from about $10^9$ to about $10^{10}$ minicells or killed bacterial cells.

16. The method of claim 14, wherein the functional nucleic acid is siRNA or miRNA.

* * * * *